United States Patent
Koenig et al.

(10) Patent No.: US 7,572,217 B1
(45) Date of Patent: Aug. 11, 2009

(54) SYSTEM AND METHOD FOR PROVIDING CARDIAC SUPPORT AND PROMOTING MYOCARDIAL RECOVERY

(75) Inventors: Steven C. Koenig, Floyds Knobs, IN (US); Guruprasad A. Giridharan, Louisville, KY (US); Kenneth N. Litwak, Louisville, KY (US); Jacob Glower, Fargo, ND (US); Daniel L. Ewert, Lake Park, MN (US)

(73) Assignees: University of Louisville Research Foundation, Inc., Louisville, KY (US); NDSU Research Foundation, Fargo, ND (US)

( * ) Notice: Subject to any disclaimer, the term of this patent is extended or adjusted under 35 U.S.C. 154(b) by 329 days.

(21) Appl. No.: 11/152,872

(22) Filed: Jun. 15, 2005

Related U.S. Application Data

(60) Provisional application No. 60/579,712, filed on Jun. 15, 2004.

(51) Int. Cl.
A61M 5/00 (2006.01)
(52) U.S. Cl. ..................................................... 600/16
(58) Field of Classification Search ............. 600/16–18; 623/3.21
See application file for complete search history.

(56) References Cited

U.S. PATENT DOCUMENTS

| | | | | |
|---|---|---|---|---|
| 5,282,849 A | * | 2/1994 | Kolff et al. | 623/3.25 |
| 5,332,403 A | * | 7/1994 | Kolff | 623/3.21 |
| 5,904,666 A | * | 5/1999 | DeDecker et al. | 604/65 |
| 5,980,448 A | * | 11/1999 | Heilman et al. | 600/16 |
| 6,132,363 A | * | 10/2000 | Freed et al. | 600/16 |
| 6,511,413 B2 | * | 1/2003 | Landesberg | 600/17 |
| 6,685,621 B2 | | 2/2004 | Bolling et al. | |
| 6,863,670 B2 | | 3/2005 | Zheng et al. | |
| 7,066,874 B2 | * | 6/2006 | Riebman et al. | 600/16 |
| 2002/0173695 A1 | * | 11/2002 | Skliar et al. | 600/16 |
| 2004/0102675 A1 | * | 5/2004 | Peters et al. | 600/16 |
| 2004/0111006 A1 | * | 6/2004 | Alferness et al. | 600/16 |
| 2005/0096496 A1 | | 5/2005 | Spence | |

OTHER PUBLICATIONS

Giridharan et al., "Left Ventricular and Myocardial Perfusion Respnses to Volume Unloading and Afterload Reduction in a Computer Simulation," ASAIO Journal, 2004, pp. 512-518, Lippincott Williams & Wilkins, Baltimore, MD.

(Continued)

*Primary Examiner*—Scott M Getzow
(74) *Attorney, Agent, or Firm*—Stites & Harbison, PLLC; David W. Nagle, Jr.; Mandy W. Decker

(57) ABSTRACT

A system for providing cardiac support to a patient and for promoting myocardial repair and recovery, comprises a device for connecting to a vasculature of the patient and a control module. The device includes a pump, defining a blood-receiving volume, and a cannula, in fluid communication with the blood-receiving volume, for anatomizing to the vasculature of the patient such that the blood-receiving volume may receive blood from and return blood to the vasculature of the patient through the cannula. The control module is for controlling the device and includes a means for establishing user-defined parameters, and a means for operating the pump of the device, which is in communication with the means for establishing user-defined parameters such that the operation of the pump is in response to the established user-defined parameters.

27 Claims, 14 Drawing Sheets

OTHER PUBLICATIONS

Glower et al., "In Vitro Evaluation of Control Strategies for an Artificial Vasculature Device," Proc. of the 26th Annual International Conference of the IEEE EMBS, Sep. 1-5, 2004, pp. 3773-3776, San Francisco, CA.

Koenig et al, "Hemodynamic and Left Ventricular Pressure-Volume Responses to Counterpulsation in Mock Circulation and Acute Large Animal Models," Proc. of the 26th Annual International Conference of the IEEE, EMBS, Sep. 1-5, 2004, pp. 3761-3764, San Francisco, CA.

Koenig et al, "Counterpulsation Therapy to Promote Myocardial Recovery," Abstract, presented at the Gordon Conference, Aug. 21-25, 2005.

Koenig et al, "Counterpulsation Therapy to Promote Myocardial Recovery," Abstract, presented at the ASAIO Conference, Washington, DC, Jun. 9-12, 2005.

Giridharan et al., "Control Strategy for an Artificual Faxcular Unloading Device," Poster, Presented at 50th ASAIO Conference, Washington, DC, Jun. 17-19, 2004.

* cited by examiner

☐ = Resistance and compliance achievable with pneumatic valve

= Resistance and compliance achievable without pneumatic valve

Cn = Compliance offered by the body

Rn = Resistance offered by the body

SYSTEM AND METHOD FOR PROVIDING CARDIAC SUPPORT AND PROMOTING MYOCARDIAL RECOVERY

CROSS REFERENCE TO RELATED APPLICATION

This application claims priority from U.S. Provisional Application Ser. No. 60/579,712 filed Jun. 15, 2004, the entire disclosure of which is incorporated herein by this reference.

GOVERNMENT SUPPORT

Research for this invention was made with support from the Whitaker Foundation Grant Number RG-01-0310.

FIELD OF THE INVENTION

The present invention relates to systems for providing cardiac support, and, more particularly, to systems for promoting myocardial repair and recovery.

BACKGROUND OF THE INVENTION

Congestive heart failure is the largest unsolved problem in cardiac care today. The incidence of congestive heart failure (CHF) is increasing worldwide with over one million new cases diagnosed annually. There are over 5.5 million people in the United States with CHF diagnosis and the number of patients is expected to double over the course of this decade.

Treatment options for CHF are limited and fall into two categories; pharmacological and mechanical. The existing treatment options only relieve the clinical symptoms of CHF and ultimately, CHF patients treated with pharmacological therapies will degenerate into the terminal phase of end-stage heart failure, for which the only therapy is cardiac transplantation. Cardiac transplantations are limited by donor scarcity to only about 2,000 procedures per year. Due to the limitation of donor organs and a long waiting list, ventricular assist devices (VAD) were introduced as a bridge to transplantation.

A VAD may be generally described as a pump that assumes the function of a damaged ventricle of the heart by uploading ventricular volume while restoring blood flow to the vasculature. In the case of a VAD designed to assist the left ventricle in pumping blood from the heart, through the aorta to the rest of the body, implantation is achieved by cannulating the apex of the left ventricle and the aorta. The VAD then assists in pumping blood from the left ventricle, through the cannula, and to the aorta.

Although VADs have traditionally been used as a bridge for patients awaiting a heart transplant, more recently, they have been tested as an alternative to heart transplantation, and the FDA has granted limited approval to permanently implanting certain VADs in qualifying patients. When used as an alternative to a heart transplant, the focus of the treatment is to facilitate recovery by allowing the weakened heart to rest. It has been reported recently that, of a series of 12 patients supported by VAD, 11 patients had myocardial recovery, and the device was successfully explanted. See Tansley, P. and M. Yacoub, "Minimally invasive explanation of totally implantable left ventricular assist devices," J. Thor. Card. Surg., 124:189-191, 2002.

Although the use of VADs as an alternative to heart transplantation is an exciting development, there are problems associated with VADs when used as an alternative to heart transplantation. For example, VADs are not designed to promote myocardial recovery and the implantation of VADs, which requires ventricular cannulation, often damages and creates loss of the myocardial tissue. For another example, aortic valve fusion can occur during chronic VAD implantation. For another example, VADs are designed to take over the pumping of blood and to do so in a continuous manner. As such, the VADs do not allow the heart to fill and eject a normal stroke volume (SV) or the amount of blood pumped by the left ventricle of the heart in one contraction. When the heart is kept from filling and ejecting a normal SV stiffening of the myocardium may result.

Another treatment option that has enjoyed some success for short-term treatment of cardiac dysfunction is counterpulsation therapy. One type of counterpulsation therapy involves removing blood from the aorta during native heart systole, thereby decreasing workload of the heart in ejecting blood, and returning the blood to the aorta as during diastole, while the heart is relaxing, thereby improving blood flow by supplying increased blood pressure during diastole. As such, counterpulsation has many important clinical benefits for the heart, including, decreased ventricular workload and increased coronary perfusion.

Counterpuslation therapy is typically provided with an intra-aortic balloon pump (IABP). Approximately 160,000 patients receive this treatment annually worldwide; however, the IABP has various disadvantages. For example, the IABP generally includes a balloon on a catheter, which catheter is introduced to the patient via a major groin artery, requiring a patient to remain supine and virtually immobilized for the duration of therapy, which results in additional complications such as muscle deterioration, clotting in the legs, and an increased risk of pneumonia. Furthermore, bacteria are found in large amounts in the groin area and bacteria may travel through the catheter and into the blood stream of the patient, causing infection. Additionally, there is a risk that the catheter introduced via the groin artery may result in blocked or substantially reduced blood flow to the patent's leg such that leg ischemia and even leg loss becomes a risk after only a few days. In any event, the application of IABP is limited to short durations, typically less than 14 days. Also, the ability to control and adjust the operation of the IABP is minimal. Accordingly, there remains a need in the art for a system and method which satisfactorily addresses the problems associated with known cardiac treatment options.

SUMMARY OF THE INVENTION

The present invention addresses the above-identified problems, and others, by providing a system and method for providing cardiac support, which is designed to promote myocardial repair and recovery by controlling aortic pressure and ventricular workload.

The system of the present invention includes an artificial vasculature device ("AVD") and a control module for controlling and adjusting the operation of the AVD. The AVD is adapted to fill with blood during native heart systole and return blood to the native vasculature during diastole in accordance with certain user-defined parameters, thereby providing counterpulsation therapy. The control module is used to set and adjust one or more of the user-defined parameters to affect control of the AVD. The user-defined parameters may include: impedance or afterload that the left ventricle must overcome during ventricular systole; timing of the filling and ejection of the device; morphology of the filling and ejection of the device (or shape of the ejection profile); rate of change of pressure during filling and ejection of the device; stroke volume or volume accepted and ejected by the device; rate of change of volume accepted and ejected by the device; and/or ratio of the number of assisted heart beats to the total number of heart beats, e.g., 1:1; 1:2.

An AVD of an exemplary system of the present invention includes a pump, a cannula, and a fluid line. The AVD communicates with the control module via the fluid line and communicates with the vasculature of the patient via the cannula. The pump includes a piston (not shown), defining a blood-receiving volume on a side of the piston in fluid communication with the cannula. The volume on the other side of the piston is in fluid communication with the fluid line.

A control module of the exemplary system of the present invention includes a driver, a motor, a controller, a computer and a user input. The controller is operative to receive user-defined parameters from the user input, and to generate a motor control signal to the motor. The motor operates the driver to deliver metered pulses of compressed air or other fluid to the pump of the AVD via the fluid line. Volume displacement in the pump is controlled by the pulses of compressed fluid. The control module also includes a pressure sensor and a flow sensor, for directly measuring the actual pressure and flow of the blood of the patient, and a valve for controlling the flow of blood downstream of the AVD.

The system of the present invention may be operated in the following manner. The AVD may be implanted in a patient by anastomosis of the cannula to the aortic arch, or to any major artery branching from the aorta or to the aorta itself. At the same time that the AVD is implanted, the valve may be implanted downstream of the AVD and the sensors may be implanted at the root of the aorta or other location adjacent the anastomosis of the AVD to the vasculature.

The flow of blood through the patient's vasculature and the implanted exemplary AVD and system of the present invention will now be described. The blood flows from the left ventricle of the heart, through the aortic valve. A first volume of blood moves via the cannula into the AVD, and a second volume moves out of the AVD via the cannula, through the valve and through the aorta to the body of the patient.

The control module of the exemplary system operates in the following manner. A user inputs certain user-defined parameters or set-points into the controller through user input. The controller generates a motor control signal in response to receiving the user-defined parameters and outputs the motor control signal to the motor. The motor and driver cooperate to deliver metered pulses of fluid to the pump of the AVD. Thus, the controller controls the fill and ejection of blood by the AVD. As the AVD operates, the sensors collect pressure and flow data, reporting them to the computer. Given the user-defined parameters and data obtained from the sensors, the computer generates an error by comparing the desired parameter values with the measured or actual parameter values and communicates the error signal to the controller. The controller may then adjust the motor-control signal to compensate for any error, such that the actual parameter values ultimately approach and substantially equal the user-defined or desired parameter values.

The system of the present invention is triggered by and responds to the action of the patient's heart. The filling of the AVD is initiated and completed when the left ventricle is in systole, and the ejection of the AVD is initiated and completed when the left ventricle is in diastole. As such, the heart ejects a stroke volume (SV) via the aortic arch into the AVD, which has been programmed by the control module to produce a desired afterload during ventricular ejection. The afterload created by the AVD may be defined by an input impedance profile, in which vascular resistance, compliance, and/or inertial elements can be controlled and adjusted to optimize the myocardial recovery process.

DETAILED DESCRIPTION OF THE INVENTION

The present invention is a system and method for providing long-term cardiac support and counterpulsation therapy, which is designed to promote myocardial repair and recovery by controlling aortic pressure and ventricular workload. The system of the present invention includes an artificial vasculature device ("AVD") and a control module for controlling and adjusting the operation of the AVD. The AVD is adapted to fill with blood during native heart systole and return blood to the native vasculature during diastole in accordance with certain user-defined parameters, thereby providing counterpulsation therapy. The control module is used to set and adjust one or more of the user-defined parameters to affect control of the AVD. The user-defined parameters may include impedance or afterload that the left ventricle must overcome during ventricular systole. Afterload is the force the heart muscle must overcome in order to eject blood into the aorta. A user may define an impedance value, a single value of impedance that does not change during the heart beat, or an impedance profile, which is a more complex, time varying function of impedance that changes in value during the span of a heart beat.

Examples of other user-defined parameters include: timing of the filling and ejection of the device; morphology of the filling and ejection of the device (or shape of the ejection profile); rate of change of pressure during filling and ejection of the device; stroke volume or volume accepted and ejected by the device; rate of change of volume accepted and ejected by the device; and ratio of the number of assisted heart beats to the total number of heart beats, e.g., 1:1; 1:2.

Figure 1:
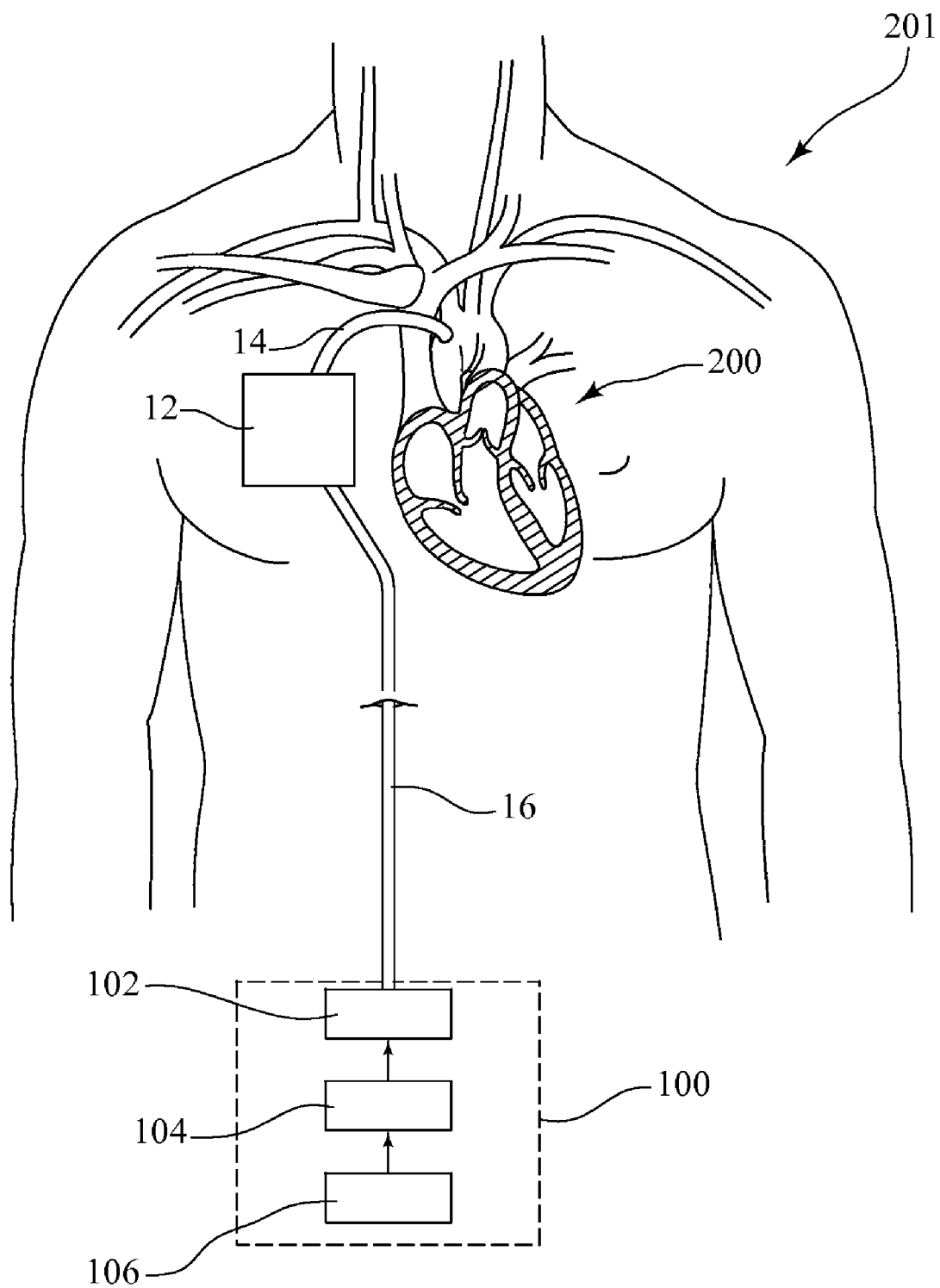
FIG. 1 illustrates the placement of an implanted exemplary artificial vasculature device (AVD) and an exemplary control module made in accordance with the present invention.
Figure 2:
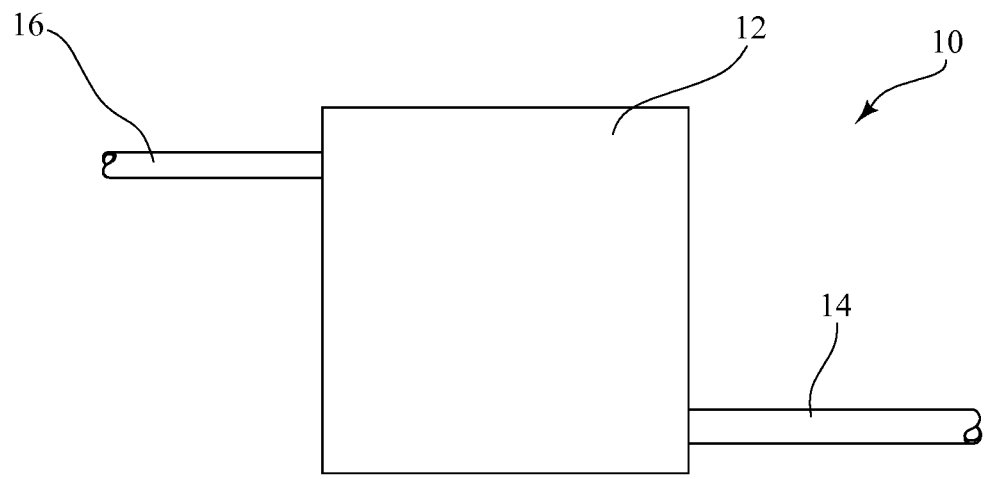
FIG. 2 is a schematic view of an exemplary AVD made in accordance with the present invention.

With reference to FIGS. 1 and 2, the AVD 10 of an exemplary system made in accordance with the present invention includes a pump 12, a cannula 14, and a fluid line 16. The AVD 10 communicates with the control module 100 via the fluid line 16 and communicates with the vasculature of the patient 201 via the cannula 14. The pump 12 may include a piston, membrane, diaphragm or similar element (not shown), defining a blood-receiving volume on a side of the piston in fluid communication with the cannula 14. The volume on the other side of the piston is in fluid communication with the fluid line 16.

The AVD 10 should be made from a material that has acceptable blood-compatibility characteristics and can be safely implanted into a patient's body 201. For example, the AVD 10 may be made from polyurethane. The blood-contacting areas of the AVD 10 are designed to be void of any flow obstructions or stagnation, sharp edges, non-washout areas and other potential thrombus-formation areas. The microscopic structure of the blood-contacting surfaces is obtained by a thermoforming technique and bonding procedure, which results in a surface structure that is homogenic and antithrombotic. Various pulsatile blood pump devices may be obtained and modified to function as an AVD of the present invention, for example, a blood pump may be obtained from Mecora Medizintechnik GmbH (Mecora Medical Technology, Aachen, Germany) and modified to provide an exemplary AVD. The modification result in the ability to control flow into and out of the device and other operations of the device, i.e., operation based on user-defined parameters.

Figure 3:
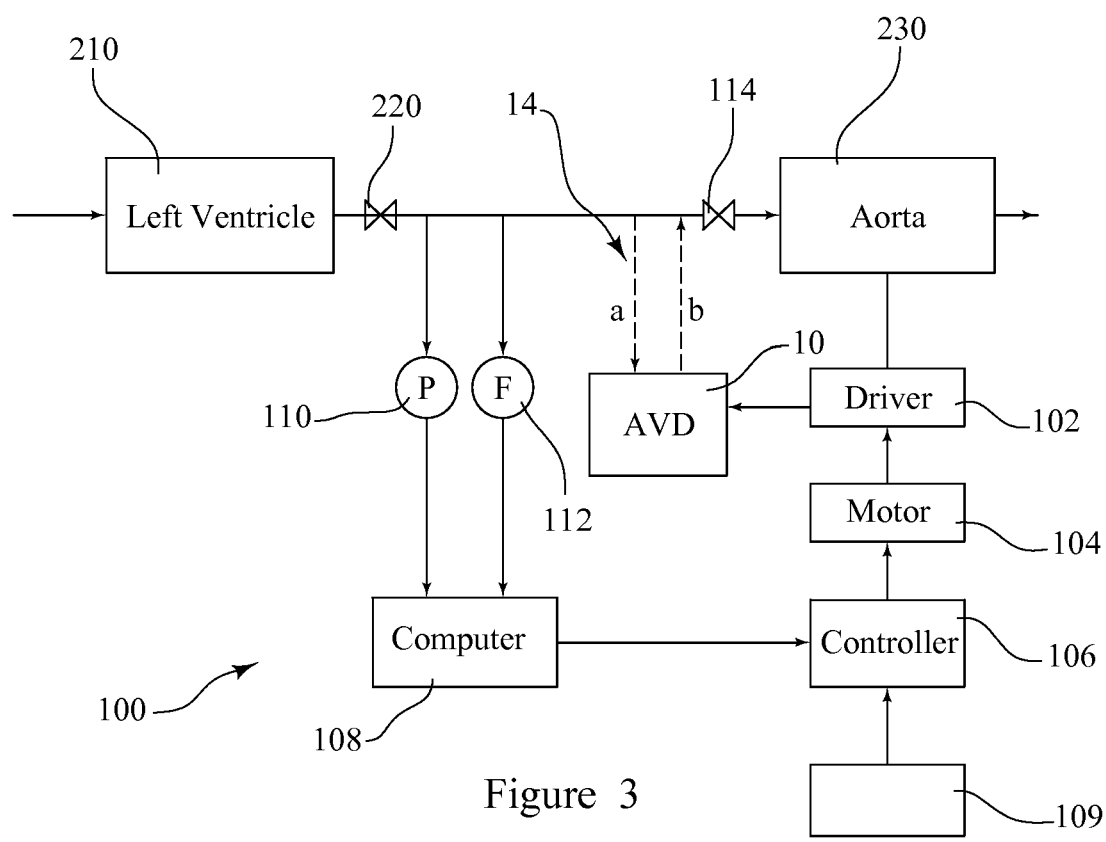
FIG. 3 is schematic view of an implanted exemplary AVD and an exemplary control module made in accordance with the present invention.

With reference to FIGS. 1 and 3, an exemplary control module 100 of the present invention includes a driver 102, a motor 104, a controller 106, a computer 108 and a user input 109. The controller 106 is operative to receive user-defined parameters from the user input 109, and to generate a motor control signal to the motor 104. The motor 104 operates the driver 102 to deliver metered pulses of compressed air or other fluid to the pump 12 of the AVD 10 via the fluid line 16. Volume displacement in the pump 12 is controlled by the pulses of compressed fluid, i.e., pneumatic or hydraulic. Controlled levels of vacuum may also be applied through the fluid line 16 to further facilitate control of the AVD 10. In other embodiments of the present invention, other means may be provided to operate the pump; for example, an actuator may be provided for sending electrical signals to the pump to affect operation, i.e., electromechanical action.

The exemplary control module 100 also includes a pressure sensor 110 and a flow sensor 112, for directly measuring the actual pressure and flow of the blood of the patient 201. Pressure sensors appropriate for use with the system of the present invention may be obtained from Millar Instruments (Houston, Tex.), and flow sensors appropriate for use with the system of the present invention may be obtained from Transonic Sensors, Inc. (Ithaca, N.Y.). In other embodiments of the present invention, the pressure and flow of blood may be measured by estimation and calculation, for example, using a method similar to the one described in: Giridharan G A, and Skliar M, "Physiological Control of Blood Pumps without Implantable Sensors," *Proceedings of the American Control Conference*, 471-475 (2003); and Giridharan G A, Olsen D B, and Skliar M, "Physiological control of rotary blood pumps using intrinsic pump parameters," 10*th Congress of the International Society of Rotary Blood Pumps*, Osaka, Japan, (2002), each of which is incorporated herein by this reference.

The exemplary control module 100 further includes a valve 114 for controlling the flow of blood downstream of the AVD 10. Valves appropriate for use with the system of the present invention include passive natural valves, passive artificial valves, and active artificial valves. Passive natural valves are obtained from an animal, for example, a valve take from a horse, calf or pig could be used. Passive artificial valves open and close in response to the difference in pressures upstream and downstream of the valve. The St. Jude Valve is an example of a passive artificial valve that may be used. (St. Jude Medical, St. Paul, Minn.). Any valve that may be used for aortic or mitral valve replacement could also be used with the system of the present invention. Active artificial valves open and close in response to a signal from a controller; for example, a pneumatic valve may be used.

With continued reference to FIGS. 1 and 3, the system of the present invention may be operated in the following manner. The AVD 10 may be implanted in a patient 201 by anastomosis of the cannula 14 to the aortic arch, or to any major artery branching from the aorta or to the aorta itself. The procedure for implanting the AVD 10 does not require any surgery to be performed on the native heart, as only cannulation to the aorta is required. As such, the risk of inflicting additional damage to the myocardium through surgery is eliminated. This implantation procedure is in contrast to the typical procedure used to implant devices such as Vascular Assist Devices (VAD), which involves ventricular apical cannulation. As such, the operative procedures for implanting and subsequently removing the AVD 10 are simplified, compared to implantation and explanation of other devices, such as VADs. At the same time that the AVD 10 is implanted, the valve 114 may be implanted downstream of the AVD 10 and the sensors 110, 112 may be implanted at the root of the aorta or other location adjacent the anastomosis of the AVD 10 to the vasculature or to the device cannula.

With reference to FIG. 3, the flow of blood through the patient's vasculature and the implanted exemplary AVD and system of the present invention will now be described. The blood flows from the left ventricle 210 of the heart 200, through the aortic valve 220. A first volume (a) of blood moves via the cannula 14 into the AVD 10, and a second volume (b), which may equal or differ from the first volume (a), moves out of the AVD 10 via the cannula 14, through the valve 114 and through the aorta 230 to the body of the patient 201.

Turning now to the flow of data through the exemplary system, with continued reference to FIG. 3, a user inputs certain user-defined parameters or set-points into the controller 106 through user input 109. The controller 106 generates a motor control signal in response to receiving the user-defined parameters and outputs the motor control signal to the motor 104. As previously described, the motor and driver cooperate to deliver metered pulses of fluid to the pump 12 of the AVD 10. Thus, the controller controls the fill and ejection of blood by the AVD 10. As the AVD 10 operates, the sensors 110, 112 collect pressure and flow data, reporting them to the computer 108. Given the user-defined parameters and data obtained from the sensors 110, 112, the computer 108 generates an error by comparing the desired parameter values with the measured or actual parameter values and communicates the error signal to the controller 106. The controller 106 may then adjust the motor-control signal to compensate for any error, such that the actual parameter values ultimately approach and substantially equal the user-defined or desired parameter values. In other embodiments of the present invention, other means for establishing user-defined parameters may be provided, as long as the means allow for the user-defined parameters to be input and allow for the communication with the means for operating the pump such that the operation of the pump is in response to the established user-defined parameters.

The system of the present invention is triggered by and responds to the action of the patient's heart 200. The filling of the AVD 10 is initiated and completed when the left ventricle is in systole, and the ejection of the AVD 10 is initiated and completed when the left ventricle is in diastole. As such, the heart 200 ejects a stroke volume (SV) via the aortic arch into the AVD 10, which has been programmed by the control module 100 to produce a desired afterload during ventricular ejection. The afterload created by the AVD 10 may be defined by an input impedance profile, in which vascular resistance, compliance, and/or inertial elements can be controlled and adjusted to optimize the myocardial recovery process.

Depending on the user-defined parameters, the AVD 10 accepts a volume (a) of blood, which may include a portion of the stroke volume or the entire stroke volume ejected from the heart 200. The user-defined parameters may also direct the AVD 10 to immediately begin filling when ventricular systole begins, or a delay may be provided before filling occurs. Time delay settings may also be modified to initiate the filling of the device before the onset of ventricular systole. Likewise, the user-defined parameters may be set such that the AVD 10 ejects a volume (b) of blood immediately when ventricular diastole begins, or a delay may be provided before ejection occurs. The user-defined parameters may also be used to adjust the volume (a) accepted by the AVD 10 and the volume (b) ejected by the AVD 10. The user-defined parameters may also be set to alter the morphologies of the AVD 10 filling with volume (a) and the ejecting volume (b), i.e., shape of the filling and ejecting profiles. For example, user-defined parameters could be set such that the AVD 10 would fill with volume (a) in accordance with a linear function, and eject with volume (b) in accordance with a sinusoidal function.

The foregoing are examples of some of the user-defined parameters that may be used; additional and different parameters may be used without departing from the spirit and scope of the present invention. One or multiple user-defined parameters may be set to alter, for example, left ventricle workload, impedance or afterload seen by the left ventricle, coronary flow, aortic pressures, aortic flows, left ventricular pressures and left ventricular flows. In any event, the user-defined parameters are intended to be selected such that chances of myocardial recovery are maximized and myocardial recovery is optimized.

It is envisioned that the system of the present invention may be used in a method for promoting myocardial recovery in patients with failure by developing protocols that serve to, for example, reduce ventricular work and increase coronary flow, strengthen the myocardium, and evaluate the myocardial recovery process. A physician or other trained user may adjust the user-defined parameters to optimize recovery for a particular patient or situation. For example, the afterload or impedance experienced by the left ventricle of the patient may be adjusted to a minimum using an input impedance profile for treatment of a severely failing left ventricle. The reduced workload of the left ventricle afforded by the minimized impedance or afterload allows the left ventricle time to rest and recover. During this time, although the workload is minimized by the system of the present invention, the left ventricle is still allowed to fill and eject normal volumes of blood, which is thought to minimize the onset of myocardial stiffening. The afterload or impedance, as defined by the input impedance profile, may be gradually increased by the user as the patient's myocardial condition improves. The afterload or impedance may also be increased to assess the level of myocardial recovery.

The system of the present invention uses "pressure unloading" to reduce ventricular workload and afterload, thereby increasing myocardial perfusion. Other devices and systems, such as VADs, provide "volume unloading," which results in very small ventricular workloads and restores blood flow to the circulation. The primary difference between pressure unloading and volume unloading is that pressure unloading allows the heart to continue to fill and empty at normal end systolic and end diastolic volumes and enables the heart to continue to function at a user-defined workload.

It should be noted that the steps of operating the computer 108 and controller 106 of the control module 100 may be implemented as program code contained on a computer readable medium. Further, it should be noted that computer readable medium, as used herein, includes any medium for storing or transmitting the program code.

The present invention is further illustrated by the following specific but non-limiting examples. The following examples are prophetic, notwithstanding the numerical values, results and/or data referred to and contained in the examples.

Computer Simulation Model

Dynamic computer models of an AVD made in accordance with the present invention, a continuous flow VAD (CVAD), and a pulsatile VAD (PVAD) are developed and incorporated into a computer model of the cardiovascular system. The AVD is compared to the VADs using the model. Additionally, different exemplary strategies for controlling the AVD to achieve certain afterload or impedance values or profiles are examined using the model. These exemplary strategies include: average impedance position control (AIPC) algorithm, instantaneous impedance force feedback (IIFF) algorithm, and instantaneous impedance position control (IIPC) algorithm. In AIPC any average value of resistance or compliance is maintained during cardiac systole. In IIFF and IIPC any value or profile of resistance and compliance is maintained.

Impedance may be defined in simple terms by resistance, compliance and inertance elements. If inertance is ignored, there are two possible configurations of resistance and compliance by which impedance may be defined; namely, a configuration where the resistance and compliance elements are in series, and a configuration with the elements are in parallel. The behavior of the system varies depending on the configuration of the resistance and compliance elements. The AVD may be controlled to mimic either configuration. The first configuration may be defined by a series resistance/compliance position control algorithm, while the second configuration may be defined by a parallel resistance/compliance position control algorithm. The parallel RC configuration is also known as the Windkessel configuration.

Computer simulations are conducted to predict cardiovascular pressure and flow responses, ventricular pressure-volume loops, and vascular resistance and compliance seen by the native heart during ejection over a range of resistances and compliances and clinical cardiac test conditions, including: normal, failure and recovery. A discussion of certain control strategies may be found in Glower, J S, R C Cheng, G A Giridharan, K J Gillars, G M Pantalos, K N Litwak, D L Ewert, and S C Koenig, "In vitro Evaulation of Control Strategies for an Artificial Vasculature Device," *Proceedings of the 26th International Conference of the IEEE EMBS*, pp 3773-6 (2004).

Average Impedance Position Control (AIPC) Algorithm

Resistance is calculated as the ratio of mean systolic aortic root pressure to total systolic flow. The compliance is calculated as the ratio of mean systolic flow rate to the rate of change of AoP during cardiac systole. Given a resistance/compliance setpoint, an error signal (e) is generated by comparing the measured and desired parameter values. The controller adjusts the stroke volume of the pump for the subsequent beat to minimize the error (e).

Series Resistance/Compliance Position Control Algorithm

The relationship between the force (F) on the piston of the AVD; position (x) of the piston; velocity (x') of the piston; and acceleration (x") of the piston is given by Formula I:

$$F=mx''+bx'+kx \qquad \text{Formula I}$$

where, m is the mass of the piston, and b and k are constants. Assuming zero mass and dividing Formula I by the square of the area of cross section of the piston ($A^2$), the relationship is given by Formula II:

$$(F/A^2)=(b/A^2)x'+(k/A^2)x \qquad \text{Formula II}$$

Since the area (A) of cross section of the piston is constant, the pump volume (V) defined by the piston is equal to (A) (x), where A is area and x is position of the piston. The rate of the volume change (V') is thus equal to (A)(x'), where x' is the velocity of the piston. A valve that closes and prevents the flow of blood downstream of the pump during cardiac systole is assumed to be provided; thus, all the blood ejected from the LV goes to the AVD device. Therefore, the pressure (P) on the piston is given by Formula III:

$$P=(b/A^2)V'+(k/A^2)V \qquad \text{Formula III}$$

Resistance (R) is equal to $b/A^2$ and compliance (C) is equal to $A^2/k$; thus, the rate of change of volume (V') is given by Formula IV:

$$V'=(P/R)-(V/RC) \qquad \text{Formula IV}$$

The values for the rate of change of volume (V') and velocity of the piston (x') may be obtained by inserting into Formula IV the values for resistance (R), compliance (C) and pressure (P), which are determined from pressure and flow sensors positioned adjacent the anastomosis of the AVD, and the volume (V), which is determined a position sensor on the piston of the AVD. A position control algorithm is designed to maintain the required position at any instant to maintain the user-defined values of R and C.

Parallel Resistance/Compliance Position Control Algorithm (2 Element Windkessel Model)

The relationship between the rate of change of pressure (P'), flowrate (Q), pressure (P), resistance (R), compliance (C) and piston area (A) for a 2 element (resistance, compliance) Windkessel model can be given by Formula V:

$$P'=(Q/C)-(P/RC) \qquad \text{Formula V}$$

With a pneumatic valve that closes and prevents the flow of blood downstream of the AVD during cardiac systole, the flowrate (Q) is equal to the rate of change of volume (V'). The rate of change of pressure (P') is equal to the rate of the change of force (F') divided by area (A) of the piston, which substitutions supplies Formula VI:

$$F'=(QA/C)-(PA/RC) \qquad \text{Formula VI}$$

The instantaneous force that the piston has to deliver in order to maintain a resistance and compliance parameters with measured instantaneous values of aortic pressure and flowrate is given by Formula VI, i.e., the instantaneous impedance force feedback (IIFF) algorithm, which manipulates the force applied to the piston to control the impedance, is given by the relationship set forth in Formula VI. A force feedback control algorithm to get the desired value of force is applied. Substituting flowrate (Q) with rate of change of volume (V') Formula V can be rewritten as Formula VII:

$$V'=CP'+(P/R) \qquad \text{Formula VII}$$

A position control algorithm to get the desired value of the rate of change of piston position, $x'=V'/A$ is applied. The instantaneous impedance position control (IIPC) algorithm, which manipulates the position of the piston in the pump to control the impedance, is given by formula VII.

Description of the Computer Simulation Model

The computer simulation models are similar to those described in: Giridharan, G. A., M. Skliar, D. B. Olsen, and G. Pantalos, "Modeling and control of a brushless DC axial flow ventricular assist device." *ASAIO Journal*, 48:272-89, 2002; Giridharan, G. A. and M. Skliar, "Modeling of the human circulatory system with an axial flow ventricular assist device," In *Proceedings of the American Control Conference*, 5:3801-6, 2001; Giridharan, G. A. and M. Skliar, "Controller design for ventricular assist devices using nonlinear hybrid model for the human circulatory system," In J. B. Rawlings, B. A. Ogunnaike, and J. W. Eaton, editors, *Chemical Process Control-VI: Assessment and New Directions for Research*, volume 98:326 of AIChE Symposium Series, pages 379-83. CACHE, American Institute of Chemical Engineers, 2002; *Proceedings of Chemical Process Control-6*, Tuscon, Ariz., January 2001; Giridharan G A, D B Olsen and M Skliar, "Physiological Control of Blood Pumps with Estimated Pressure Differential with Intrinsic Pump Parameters," *Artificial Organs*, (in review); Giridharan G A and M Skliar, "Nonlinear controller for ventricular assist devices," *Artificial Organs*, 26:980-4, 2002; and Giridharan G A and M Skliar, "Control strategy for maintaining physiological perfusion with implantable rotary blood pumps," *Artificial Organs*, 27:639-48, 2003, which are incorporated herein by this reference.

Figure 4:
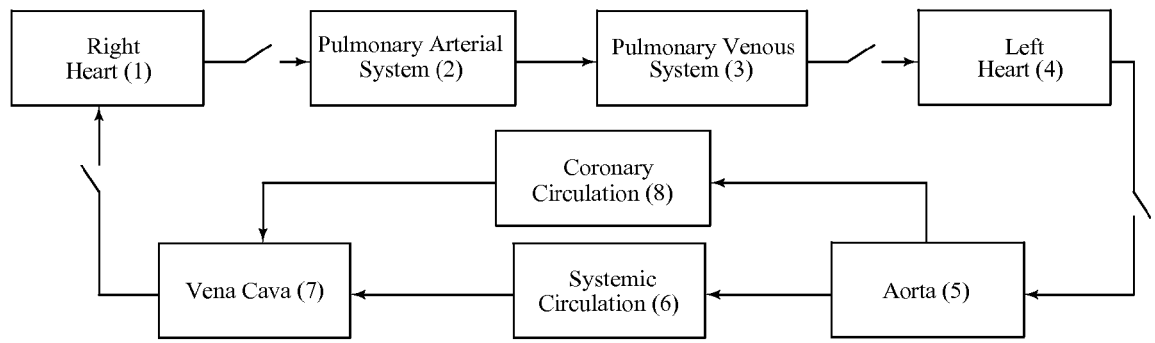
FIG. 4 is a diagram of the computer simulation model used to test the AVD of the present invention, which model includes four heart valves and at least seven parameter blocks, including: right heart, pulmonary arterial system, pulmonary venous system, left heart, aorta, systemic circulation, and vena cava.

Briefly, with reference to FIG. 4, the model subdivides the human circulatory system into an arbitrary number of lumped parameter blocks, each characterized by its own resistance, compliance, pressure and volume of blood. In its simplest configuration, the model has eleven elements: 4 heart valves and 8 blocks, including: right heart (1); pulmonary arterial system (2); Pulmonary Venous system (3); left heart (4); aorta (5); systemic circulation (7); vena cava (7) and coronary circulation (8). The baseline values for the normal, failing and recovering left heart (LH) are given in Table A.

TABLE A

| Parameter | Normal | Failure | Recovery |
|---|---|---|---|
| Aortic Pressure (AoP, mmHg) | 120.5/75.7 | 96.5/59.6 | 111/68.6 |
| Cardiac Output (CO) (l/m) | 4.77 | 3.74 | 4.35 |
| Left Heart Pressure, (LHPed) (mmHg) | 6.1 | 26.4 | 16.2 |
| Left Heart Volume (ml) | 73.6/153.1 | 217.1/279.4 | 90.9/163.3 |

The computer model of the AVD and comparison of physiologic responses of the AVD to continuous and pulsatile VAD in the computer simulation model of the cardiovascular system are described in more detail in Giridharan G A, Ewert D L, Pantalos G M, Gillars K J, Litwak K N, Gray L A, and Koenig S C, "Left ventricular unloading and myocardial perfusion responses to volume reduction in a computer simulation," *ASAIO Journal*, 50 (5): 512-518, 2004, which is incorporated herein by this reference.

Differences in characterizing hemodynamic parameter values, ventricular pressure-volume loop responses, and vascular compliance and resistance seen by the ventricle during ejection are calculated using a Hemodynamic Evaluation and Assessment Research Tool (HEART) program and supporting m-files developed in Matlab (MathWorks, Natick, Mass.). See Schroeder M J, B Perrrault, D L Ewert, and S C Koenig, "HEART: An automated beat-to-beat cardiovascular analysis package using Matlab®," *Comp. Biol. & Med.* 2005 (in press), which is incorporated herein by this reference.

Pressure, flow, and volume waveforms are used to calculate the following hemodynamic parameters: cardiac output; aortic systolic, diastolic, and mean pressures; aortic flow; vascular resistance and compliance; assist device output flow; mean, mean systolic, mean diastolic, peak systolic and peak diastolic left main coronary flow (CoF); and the ratio of mean diastolic to mean systolic CoF.

Figure 5A:
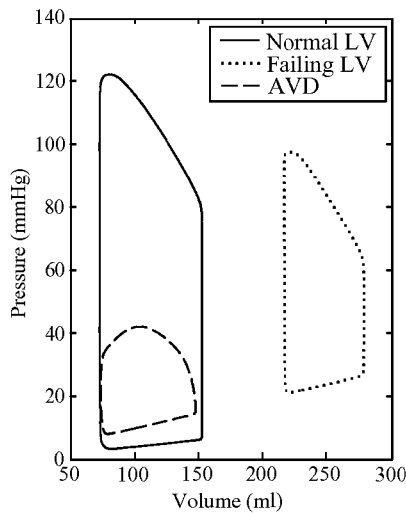
FIG. 5A is a graph comparing the pressure-volume loops of a normal and failing left ventricle (LV) with and without assistance from the AVD of the present invention.
Figure 5B:
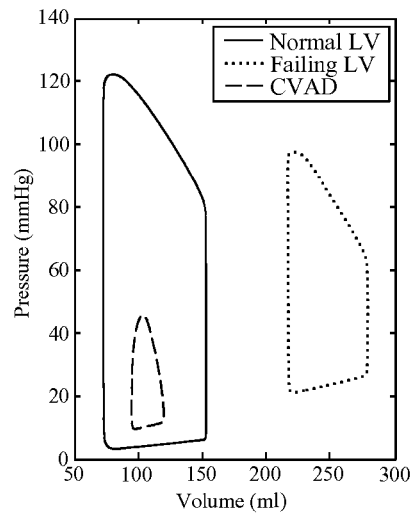
FIG. 5B is a graph comparing the pressure-volume loops of a normal and failing left ventricle (LV) with and without assistance from a continuous flow VAD.
Figure 5C:
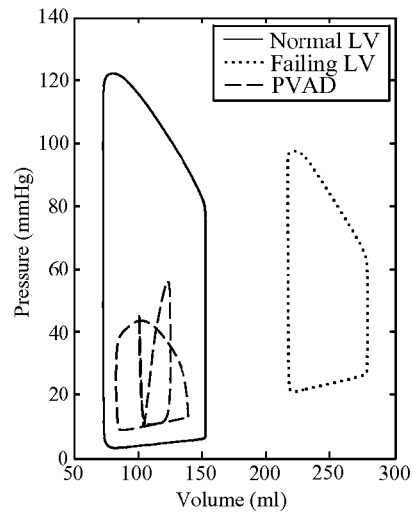
FIG. 5C is a graph comparing the pressure-volume loops of a normal and failing left ventricle (LV) with and without assistance from a pulsatile VAD.

With regard to comparing the AVD to the VADs, pressure-volume loops are constructed by plotting ventricular pressure against ventricular volume. With reference to FIGS. 5A-5C, pressure-volume loops are constructed for normal left ventrical (normal LV), failing left ventrical without assistance (failing LV), and failing left ventrical assisted by the AVD, the continuous VAD (CVAD), or pulsatile VAD (PVAD). The comparison of the pressure-volume loops indicate that the AVD enables the heart to fill and eject at normal end-systolic and end-diastolic volumes.

The computer simulation study demonstrates several advantages of the AVD, including better diastolic coronary augmentation and reduced vascular resistance and elastance. Since almost all of the endocardial perfusion takes place during cardiac diastole, by counterpulsation, the device of the present invention promotes diastolic flow and presumably improves endocardial perfusion. In the simulation study, the device of the present invention produces up to about 25% higher diastolic flow compared to PVAD and CVAD.

Figure 6:
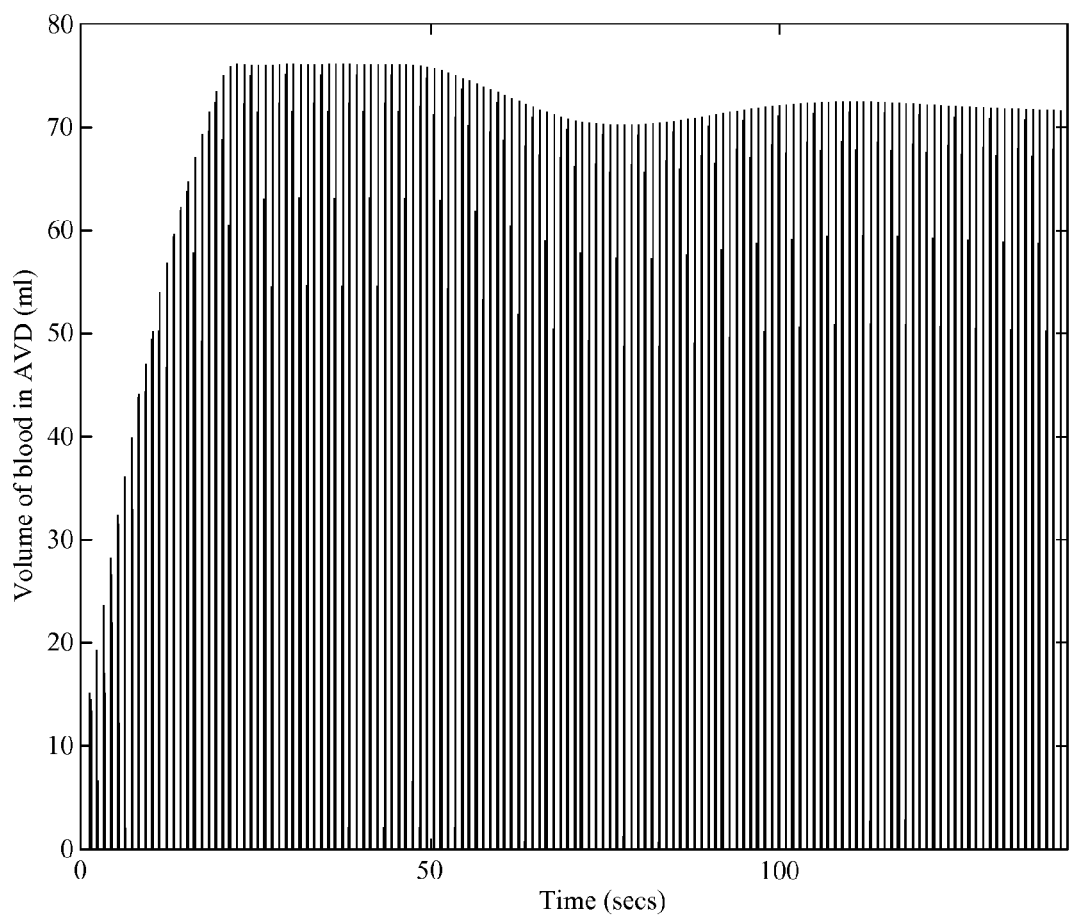
FIG. 6 is a graph showing the volume of blood in the AVD as a function of time with the average impedance position control algorithm.

With regard to controlling the AVD using the average impedance position control algorithm (AIPC), the series resistance/compliance control algorithm, and the parallel resistance/compliance control algorithm (2 element Windkessel model), the mean coronary flow (CoF) and mean diastolic CoF increases with decreasing impedance or afterload. Left ventricle (LV) volume and LV pressure decreases and LV stroke volume increases with decreasing impedance, resulting in an increased ejection fraction with average impedance, position and force feedback control algorithms. FIGS. 6 through 8 provide the simulation results with the average impedance position control algorithm.

FIG. 6 is a graph showing the volume of blood in the AVD as a function of time, indicating that the controller adjusts the stroke volume of the AVD with the AIPC algorithm.

Figure 7A:
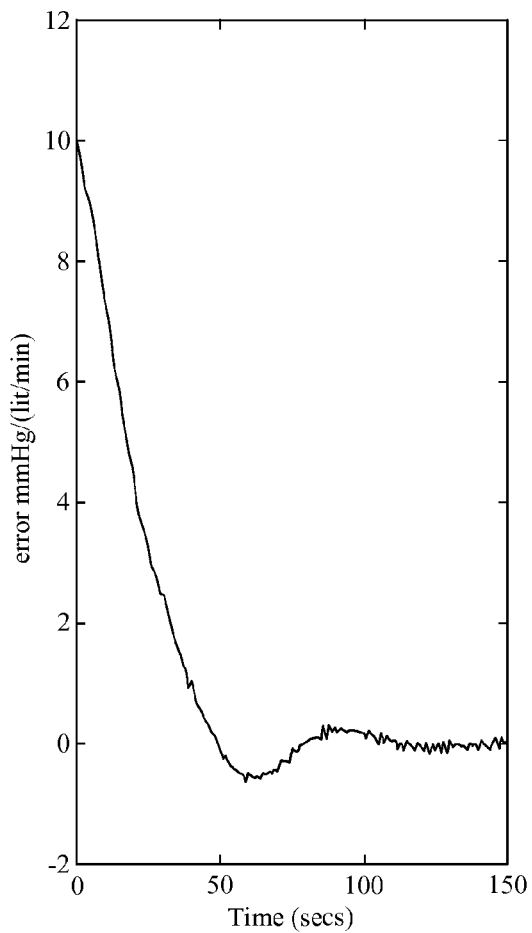
FIG. 7A is a graph showing the error (e) as a function of time with the average impedance position control algorithm.
Figure 7B:
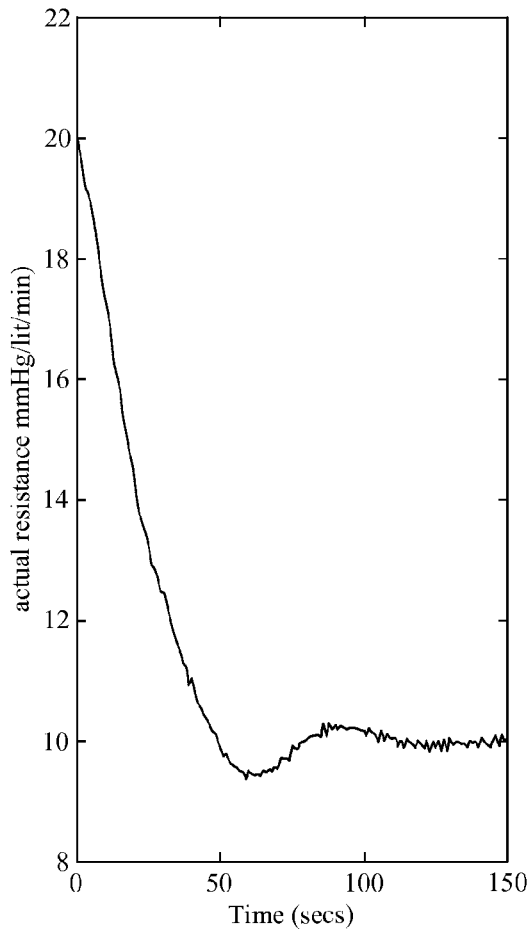
FIG. 7B is a graph showing the actual resistance as a function of time with the average impedance position control algorithm.

FIG. 7A is a graph showing the error (e) as a function of time and FIG. 7B is a graph showing the actual resistance, measured using the "implanted" sensors, as a function of time.

FIGS. 7A and 7B show that the control action reduces the resistance experienced by the left ventricle to the user-defined parameter, i.e., about 10 mmHg/(lit/min) in the example, resulting in an error of substantially zero.

Figure 8A:
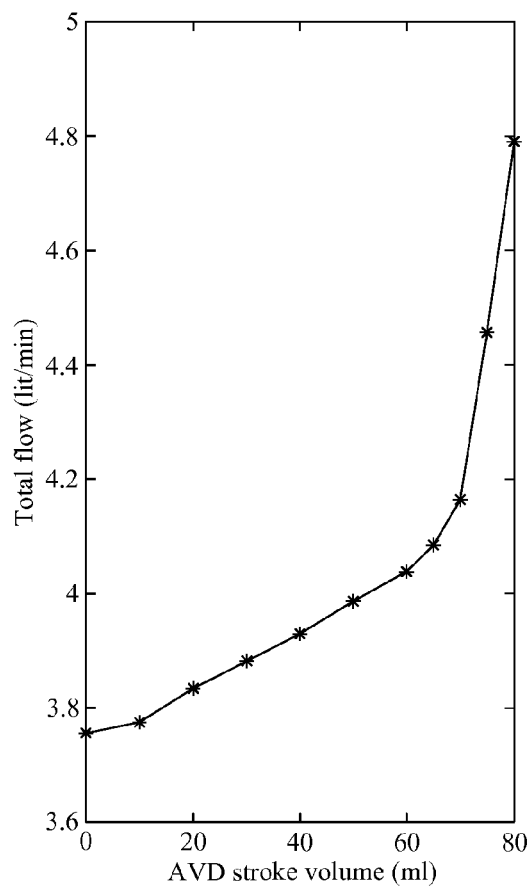
FIG. 8A is a graph showing the total flow rate as a function of AVD stroke volume with the average impedance position control algorithm.
Figure 8B:
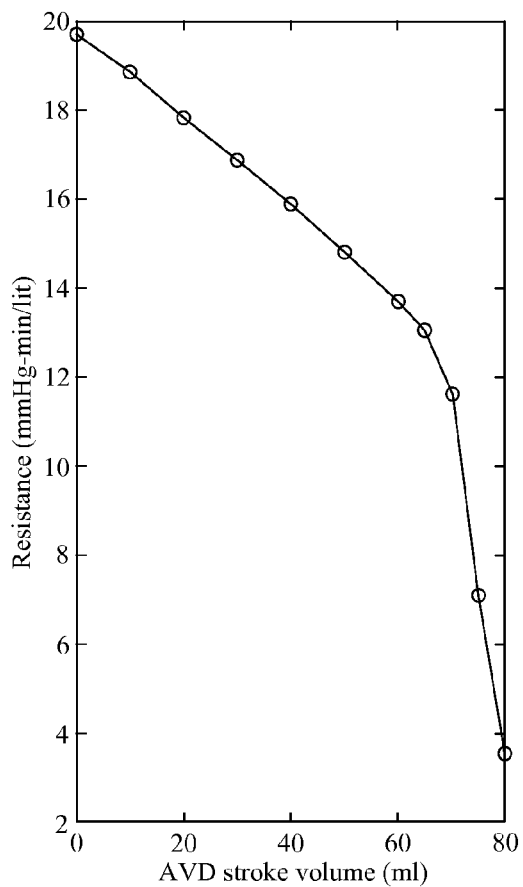
FIG. 8B is a graph showing resistance as a function of AVD stroke volume with the average impedance position control algorithm.

FIG. 8A is a graph showing the total flow rate as a function of AVD stroke volume, indicating that the resistance experienced by the left ventricle during systole reduces with increasing flow rate (stroke volume) of the AVD and the total flow rate increases with increasing AVD stroke volume. FIG. 8B is a graph showing resistance as a function of AVD stroke volume, indicating that the total flow out of the left ventricle increases with increase in AVD stroke volume.

Figure 9:
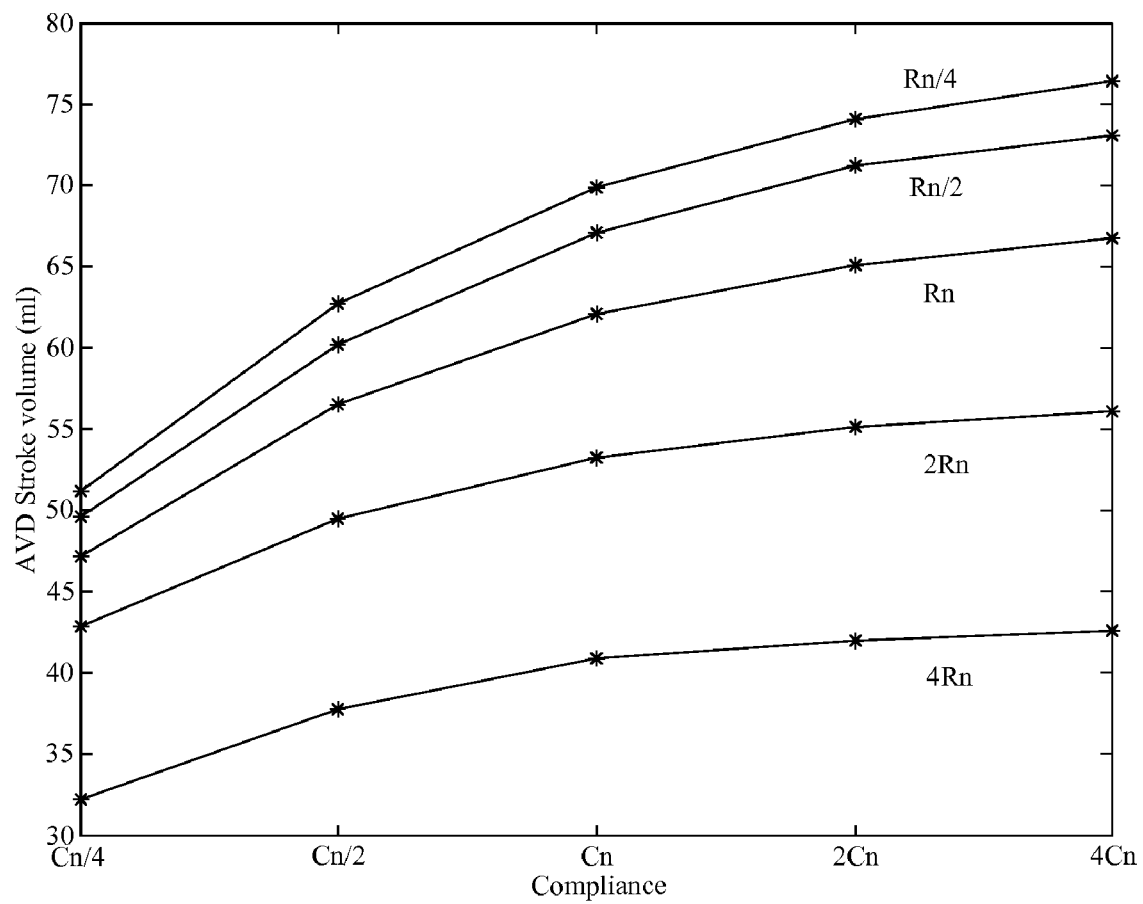
FIG. 9 is a graph showing the relationship between resistance, compliance and stroke volume of the AVD with a series resistance/compliance position control algorithm.

FIG. 9 is a graph showing the relationship between resistance, compliance and stroke volume of the AVD with a series resistance/compliance position control algorithm. Rn and Cn are the normal values of resistance and compliance of the vasculature. An increase in conductance and compliance user-defined parameters requires an increase in the steady state AVD stroke volume needed to maintain the user-defined parameters.

Figure 10A:
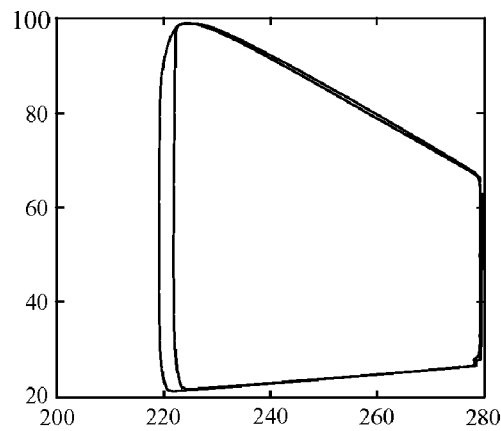
FIG. 10A depicts a pressure-volume loop in a 2 element Windkessel model for normal resistance and compliance.
Figure 10B:
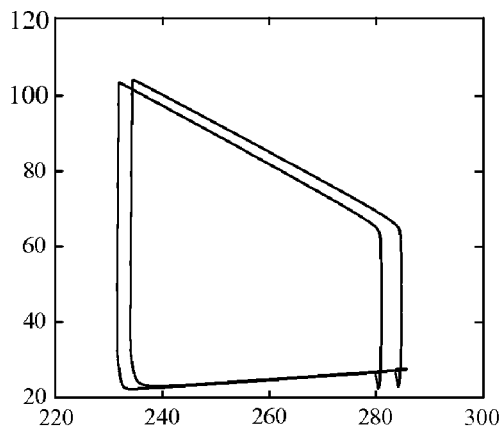
FIG. 10B depicts a pressure-volume loop in a 2 element Windkessel model for infinite resistance.
Figure 10C:
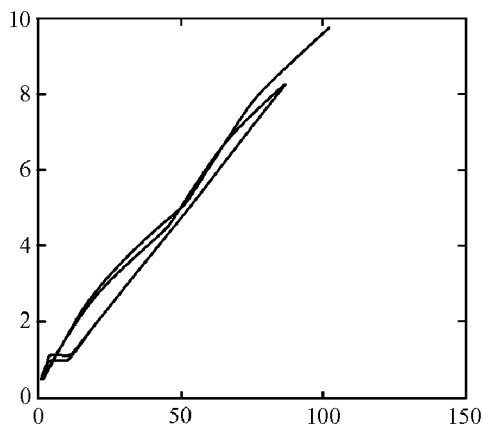
FIG. 10C depicts a pressure-volume loop in a 2 element Windkessel model for near zero resistance.
Figure 10D:
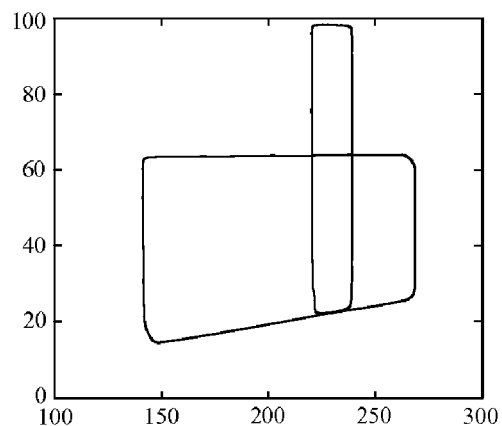
FIG. 10D depicts a pressure-volume loop in a 2 element Windkessel model for infinite compliance.
Figure 10E:
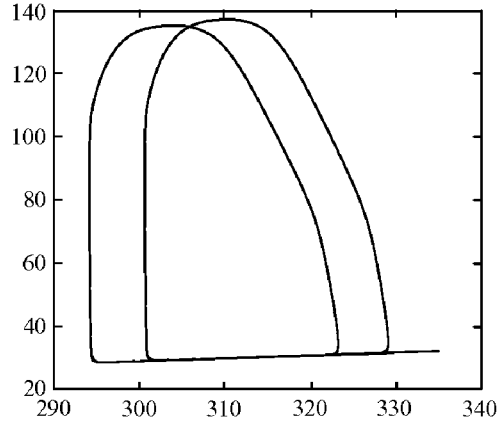
FIG. 10E depicts a pressure-volume loop in a 2 element Windkessel model for near zero compliance.
Figure 10F:
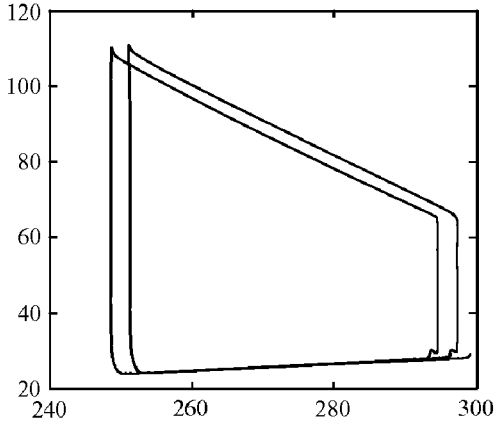
FIG. 10F depicts a pressure-volume loop in a 2 element Windkessel model for negative resistance for a failing left ventricle.

Theoretically, the AVD is capable of producing nearly any value of impedance. In the parallel resistance/compliance position control algorithm (2 element Windkessel model), the resistance and compliance are in parallel; thus, the volume can be unloaded either via the resistive element or the capacitative (compliance) element. FIGS. 10A-10F depict pressure-volume loops in a 2 element Windkessel model for normal resistance and compliance (FIG. 10A); infinite resistance (FIG. 10B); near zero resistance (FIG. 10C); infinite compliance (FIG. 10D); near zero compliance (FIG. 10E); and negative resistance for a failing left ventricle (FIG. 10F). FIG. 10A shows the pressure-volume relationship for a failing left ventricle (LV) with the AVD maintaining normal values of resistance and compliance. The LV end systolic and end diastolic volumes are more than double the normal values, and the native LV stroke volume and peak LV pressure are reduced. With the AVD maintaining an infinite resistance and a normal value of compliance, the rate of change of pressure is equal to the ratio of the flowrate over compliance, as provided by Formula V. With reference to FIGS. 10B and 10E, an infinite resistance user-defined parameter or a near zero compliance user-defined parameter results in increasing values of LV volume, peak LV pressure and LV end diastolic pressure every cardiac cycle. However, with reference to FIG. 10C, with near zero resistance and normal compliance user-defined parameter, the LV volumes and pressures reduce drastically. As shown in FIG. 10D, the LV pressure remains at a constant value when the AVD tries to maintain an infinite compliance value. The resultant PV loop is sensitive to the initial pressure condition during each systole, which can vary between each cardiac cycle. A negative resistance user-defined parameter leads to decreasing values of LV pressures and volumes.

Figure 11:
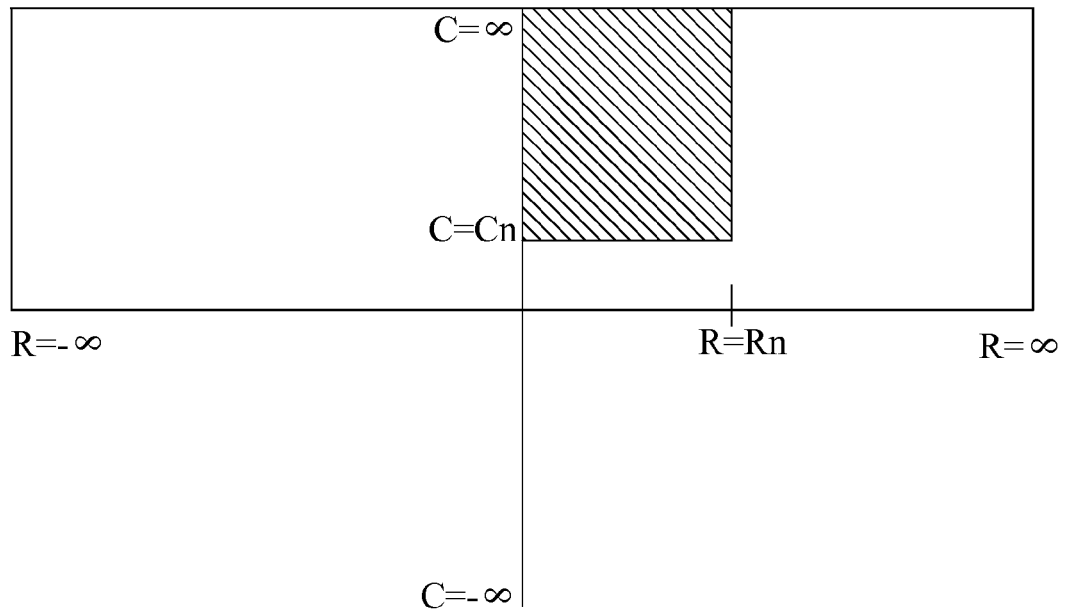
FIG. 11 is a graphic representation of the resistance and compliance values achievable with and without the valve positioned downstream of the AVD.
Figure 11:
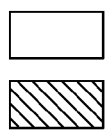

FIG. 11 is a graphic representation of the Resistance and compliance values achievable with and without the valve positioned downstream of the AVD. Though the AVD can produce any value of impedance desired, the AVD cannot produce an input impedance higher than that of the body without a pneumatic valve to prevent the flow of blood from LV to the systemic circulation during systole.

The computer simulation studies demonstrate several potential advantages of the AVD system, including better diastolic coronary flow augmentation and control of the resistance experienced by the native left ventricle (LV). The AVD provides active filling, allowing control of the afterload seen by the native ejecting LV. The ability of the AVD to produce any desired afterload may be a component to providing optimal myocardial support and the development of weaning and testing procedures. For example, the afterload may be gradually increased by gradually reducing the AVD stroke volume (SV) to strengthen the myocardium following confirmation of sufficient myocardial recovery. Further, ventricular response to a rapid increase in afterload produced by the AVD may be used as a potential measure of myocardial recovery.

The average impedance control algorithm is more resistant to measurement noise; however, instantaneous control of impedance is not achievable with the average impedance control algorithm. In contrast, the resistance/compliance (RC) series and RC parallel (2 element Windkessel) models allow for instantaneous control of resistance and compliance and are more susceptible to measurement noise from the pressure and flow sensors. In particular, the position control algorithm with the 2 element Windkessel model is most susceptible to measurement noise as the pressure measurement needs to be differentiated. Differentiation of noisy measurements leads to noise amplification. A filter can be used to minimize the noise passing through; however, filters can cause a time delay which can be detrimental to instantaneous control. The RC series model and the Windkessel model can produce any given resistance and compliance values provided a pneumatic valve is present on the downstream of the AVD device except for negative compliance which makes the system unstable, as illustrated in FIGS. 10A-10F. In the absence of a pneumatic valve, the maximum value of impedance is limited to the value of the impedance offered by the body, as illustrated in FIG. 11.

The AVD as tested in the computer simulation study allows the native heart to fill to normal volumes and eject its stroke volume (SV) through the aortic valve. The AVD's primary systolic function is to control the afterload by allowing the user to define any designed desired systemic vascular input impedance seen by the heart. The computer simulation study demonstrates that the AVD has the potential to produce greater diastolic coronary perfusion, reduce ventricular workload while continuing to enable the left ventricle to fill and eject at normal volumes, and allow the heart to eject against a lower afterload compared to continuous and asynchronous pulsatile assist techniques. It is believed that afterload reduction and myocardial training using the AVD approach will augment the myocardial recovery process. In addition to being used as a therapeutic device, the AVD device can be used as a potential research tool to study cardiovascular coupling, due to the ability to control the afterload experienced by the heart. The AVD system may be used for treatment strategies that promote myocardial recovery and testing and weaning protocols.

In Vitro Mock Circulation Model

An adult mock circulation is used to test the different strategies for controlling the AVD. The mock circulation model uses a pulse duplicator designed to mimic the AVD of the present invention. The pulse duplicator (AVD) is configured with a single cannula, for in flow and outflow. A controller is provided, which inflates during heart diastole to augment myocardial perfusion, and deflates during systole to provide afterload reduction.

The mock circulation system is similar to those described in, Koenig S C, Pantalos G M, Litwak K N, Gillars K J, Giridharan G A, Maguire M, and Spence P A, "Hemodynamic and Left Ventricular Pressure-Volume Responses to Counterpulsation in Mock Circulation and Acute Large Animal Models," *Proceedings of the 26th Annual International Conference of the IEEE EMBS*, pp. 3761-4, 2004; Pantalos G M, Koenig S C, Gillars K J, Giridharan G A, and Ewert D L, "Characterization of an adult mock circulation for testing cardiac support devices," *ASAIO Journal*, 50:37-46, 2004; Koenig S C, G P Pantalos, K J Gillars, D L Ewert, K N Litwak, and S W Etoch, "Hemodynamic responses to continuous and pulsatile assist in an adult mock circulation," *ASAIO Journal*, 50:15-24, 2004; and Koenig S C, C Woolard, G D Drew, L Unger, K J Gillars, D L Ewert, L A Gray, and G M Pantalos, "Integrated data acquisition system for medical device testing and physiology research in compliance with Good Laboratory Practices," *Biomed. Instr. & Tech.* 38(3):229-40, 2004, which are incorporated herein by this reference.

Briefly, the mock circulation model includes: atrium, ventricle vasculature, systemic vasculature, and coronary vasculature. The aortic section has conduits for the aortic arch, brachiocephalic artery, and descending abdominal aorta cannulation. The mock circulation model is tuned to produce mild and moderate heart failure conditions with mean aortic pressures (about 80 and 65 mmHg), cardiac outputs (about 4.0 and 3.0 l/m), and left ventricular end-diastolic pressures (about 5 and 15 mmHg) comparable to values reported clinically for human ventricles in normal and moderate failure states. Heart rate is 72 bpm for all test conditions. The mock circulation system is used to compare the AVD to other devices, such as an intra-aortic balloon pump (IABP). The AVD is cannulated at the aortic arch (AA), brachiocephalic artery (BA), and descending abdominal aorta (DAA), and the IABP tip positioned at the distal aortic arch. For each configuration, hemodynamic waveforms are recorded during (1) normal baseline, (2) failure baseline, (3) failure and AVD displacements of 40, 60, and 80 ml for 1:1 and 1:2, and (4) failure and IABP 40 ml inflation in 1:1 and 1:2 modes. The mock circulation study demonstrates that therapy using the AVD could effectively reduce filling pressure and afterload, and increase diastolic coronary artery flow.

Figure 12A:
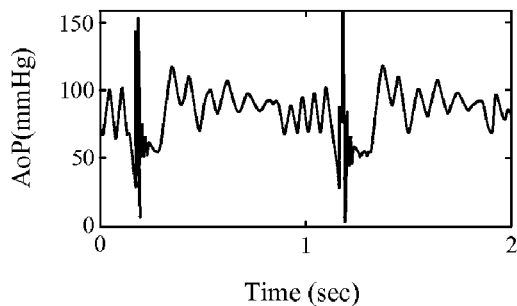
FIG. 12A is waveform showing aortic pressure (AoP) for the series RC configuration.
Figure 12B:
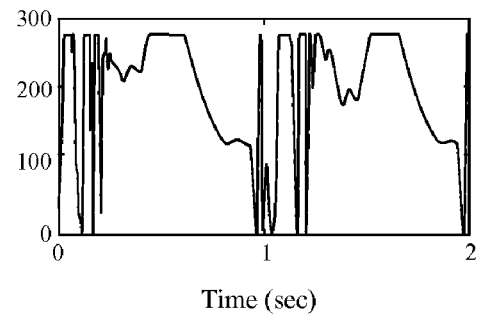
FIG. 12B is waveform showing aortic pressure (AoP) for the parallel RC configuration.
Figure 12C:
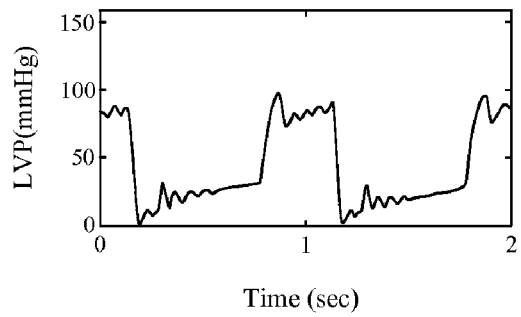
FIG. 12C is waveform showing left ventricle pressure (LVP) for the series RC configuration.
Figure 12D:
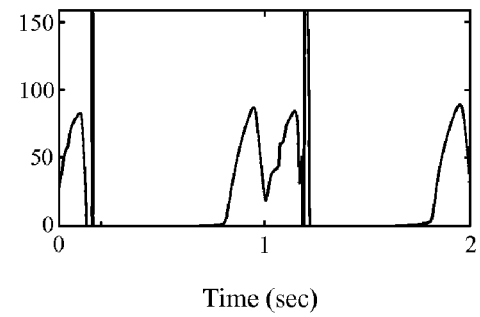
FIG. 12D is waveform showing left ventricle pressure (LVP) for the parallel RC configuration.
Figure 12E:
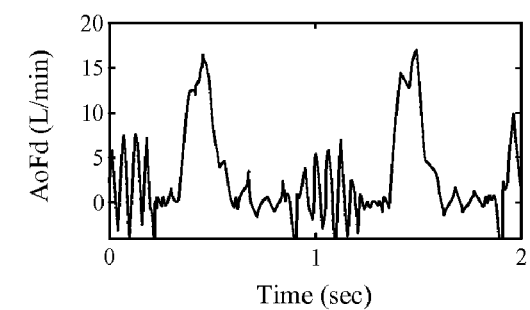
FIG. 12E is waveform showing distal aortic flow (AoFd) for the series RC configuration.
Figure 12F:
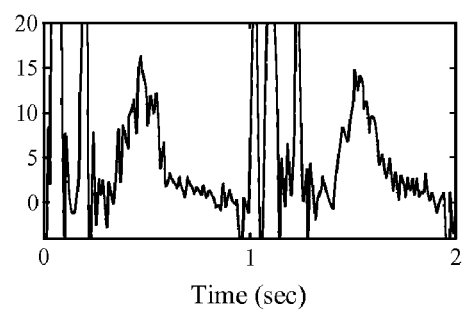
FIG. 12F is waveform showing distal aortic flow (AoFd) for the parallel RC configuration.

Pulse Duplicator (AVD) Simulation Results Using Series Resistance/Compliance and Parallel Resistance/Compliance (Windkessel) Configurations FIGS. 12A-12F are graphs showing aortic pressure (AoP), left ventricle pressure (LVP) or distal aortic flow (AoFd), as a function of time, for the series RC and parallel RC configurations. The RC series and 2-element Windkessel (RC parallel) models produce counterpulsation, as can be seen in the aortic pressure (AoP) and distal aortic flow (AoFd) waveforms, shown in FIGS. 12A and 12B. As shown in FIGS. 12C and 12D, the AVD reduces the peak systolic left ventricular pressure (LVP) for each control algorithm. Comparing FIGS. 12A, 12C and 12E to FIGS. 12B, 12D and 12F, the RC series position control algorithm is more tolerant towards measurement noises and system disturbances than the RC parallel position control algorithm.

Figure 13:
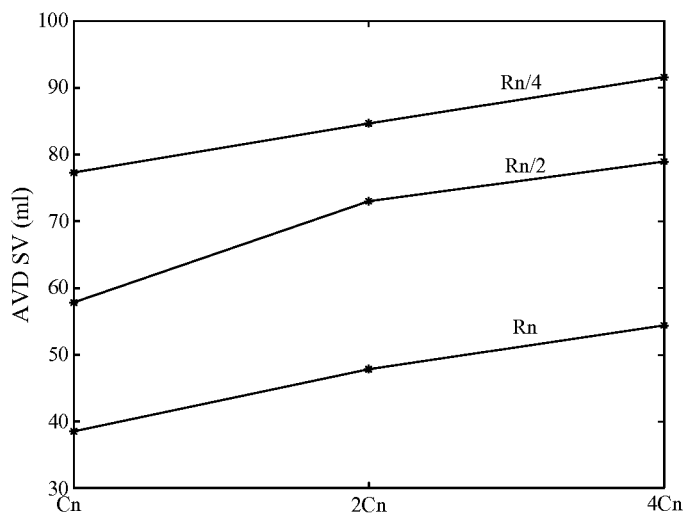
FIG. 13 is a graph showing stroke volume of the AVD as a function of resistance (R) and compliance (C), where Rn and Cn are normal clinical values.
Figure 14:
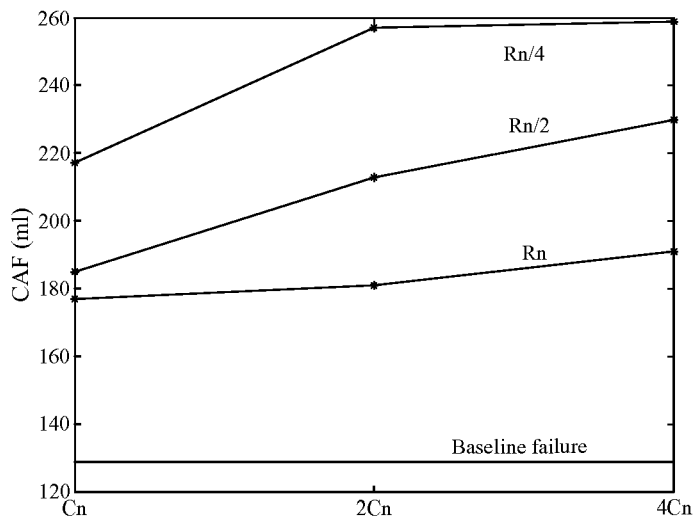
FIG. 14 is a graph showing coronary artery flow (CAF) as a function of resistance (R) and compliance (C), where Rn and Cn are normal clinical values.
Figure 15:
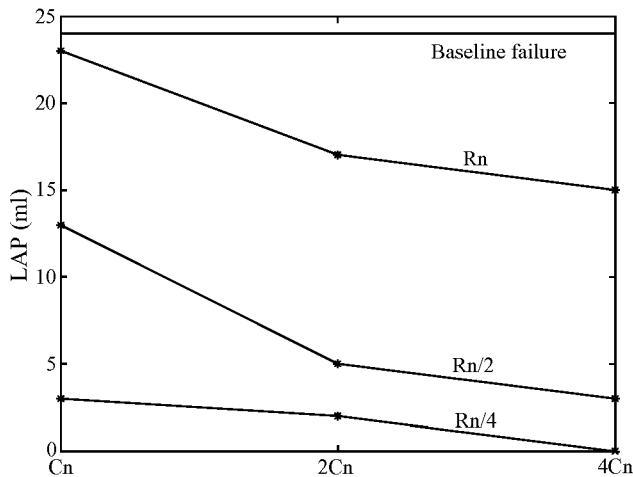
FIG. 15 is a graph showing left atrial pressure as a function of resistance (R) and compliance (C), where Rn and Cn are normal clinical values.

FIGS. 13 through 15 depict stroke volume of the AVD, coronary artery flow (CAF) and left atrial pressure (LAP) as a function of resistance (R) and compliance (C), where Rn and Cn are normal clinical values. The RC series position control algorithm increases device stroke volume (SV) and coronary artery flow (CAF) and reduces left atrial pressure (LAP) for decreasing impedance setpoints. As shown in FIG. 14, the CAF increases by up to 100% for a four-fold decrease in Rn and four-fold increase in Cn from baseline failure. As shown in FIG. 15, the AVD restores LAP during failure (about 24 mmHg) back to normal baseline (about 4 mmHg) provided selection of a suitable impedance setpoint.

Results of the In Vitro Mock Circulation Study

The mock circulation study demonstrates several potential advantages of the conceptual approach to the artificial vasculature device of the present invention, including diastolic coronary flow augmentation, reduced preload (LAP), and reduced afterload via control of the resistance and elastance experienced by the native left ventricle. The ability of the device to produce any desired afterload may assist in providing optimal myocardial support and the development of weaning and testing procedures in heart failure patients. First, ventricular response to a rapid increase in afterload produced by the device may be used as a potential measure of myocardial recovery. Following confirmation of sufficient myocardial recovery, the afterload may be gradually increased by gradually increasing the impedance setpoint of the device to strengthen the myocardium.

Large Animal Heart Failure Model

A large animal with diminished cardiac function would be useful for chronic testing of pathophysiologic responses to many human-sized devices and other therapies, especially if the model does not require prior surgical interventions or significant technical skill and expense. A clinically relevant model of diminished cardiac function (DCF) has been developed using a single, oral dose of Monensin, as described in Litwak K N, A McMahan, K A Lot, L E Lott and S C Koenig, "Monensin toxicosis in the bovine calf: a large animal model of cardiac dysfunction," *Comparative Medicine* 2005 (in press), which is incorporated herein by this reference. Monensin is a polyether ionophore antibiotic widely used in the cattle industry as a growth promotant that, when given in large quantities, can lead to cardiac toxicity. A single oral dose of Monensin (about 20 mg/kg) is given to 15 calves (about 55-90 kg) to produce a diminished cardiac function (DCF) model. Hemodynamics and cardiac geometry are monitored for up to about 21 days postinduction for portion of the calves and 90 days postinduction for another portion of the calves. Compared to similar-sized normal animals, stroke volume is about 42% lower, left atrial pressure is about 67% higher, and end-diastolic left ventricular pressure is about 143% higher.

Figure 16:
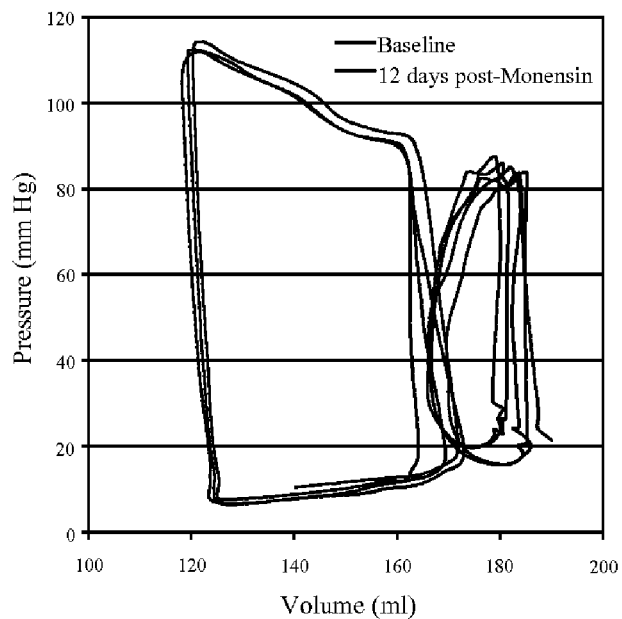
FIG. 16 is pressure-volume loop following administration to the bovine calf of about 20 mg/kg oral Monensin to create a CDF calf.

Echocardiography recordings demonstrate increased end-systolic and end-diastolic ventricular dimensions. With reference to FIG. 16, showing the left ventricular pressure-volume relationship following receipt of about 20 mg/kg oral Monensin, the treatment results in a decrease in pressure and stroke volume, with an increase in cardiac volume, which is suggestive of heart failure. Additionally, the cardiac Histopathologic analysis shows significant cardiomyocyte death. These results demonstrate that a single oral dose of Monensin provides a simple, non-invasive, inexpensive, and likely irreversible means of producing clinically relevant DCF in a human-sized animal model.

Cardiac Source Impedance

Figure 17:
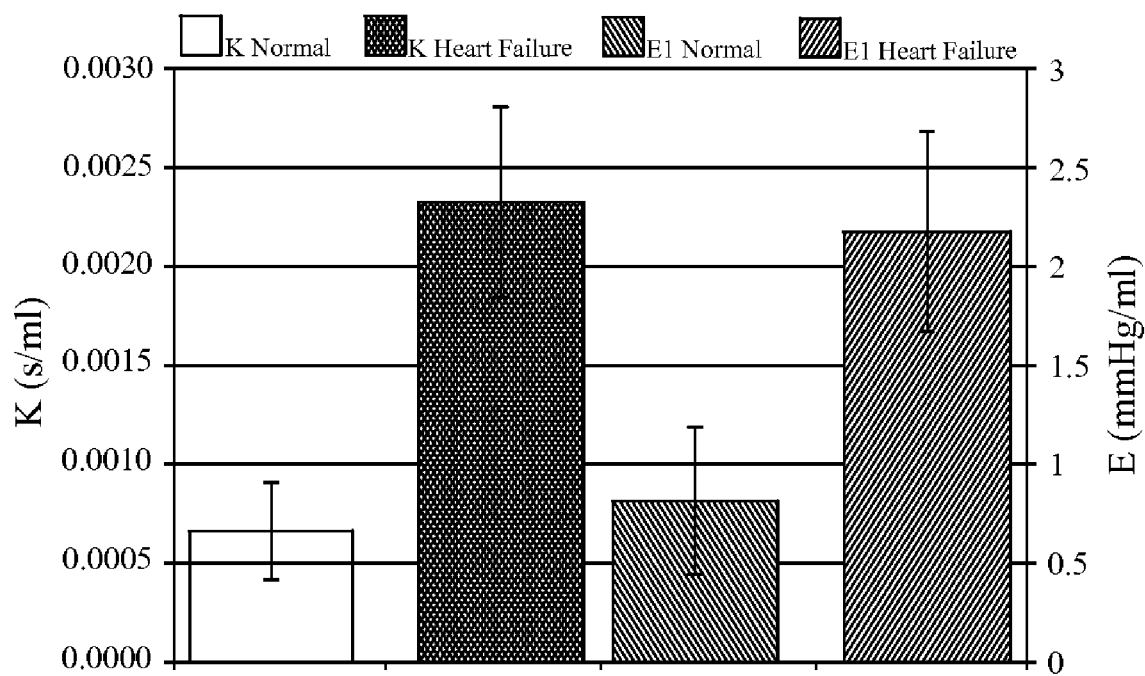
FIG. 17 is a bar graph comparing parallel elastance (E1) and the myocardial friction (K) in normal calves and DCF calves.

Data obtained in calves with normal and DCF hearts are used to calculate visco-elastic properties of the myocardium using a computational technique developed described in Ewert D L, B Wheeler, C Doetkott, C Ionan, G M Pantalo and S C Koenig, "The effect of heart rate, preload, and afterload on the visco-elastic properties of the swine myocardium, *Ann. Biomed, Eng.*, 32(9):1211-1222, 2004, which is incorporated herein by this reference. With reference to FIG. 17, in the DCF calves, the parallel elastance (E1) is about four times greater and the myocardial friction (K) is about three times greater compared to calves with normal left ventricles. This suggests that the DCF calves have diminished contractility and large frictional losses. The system of the present invention will restore the visco-elastic properties to normal ranges.

Vascular Load Impedance

Figure 18:
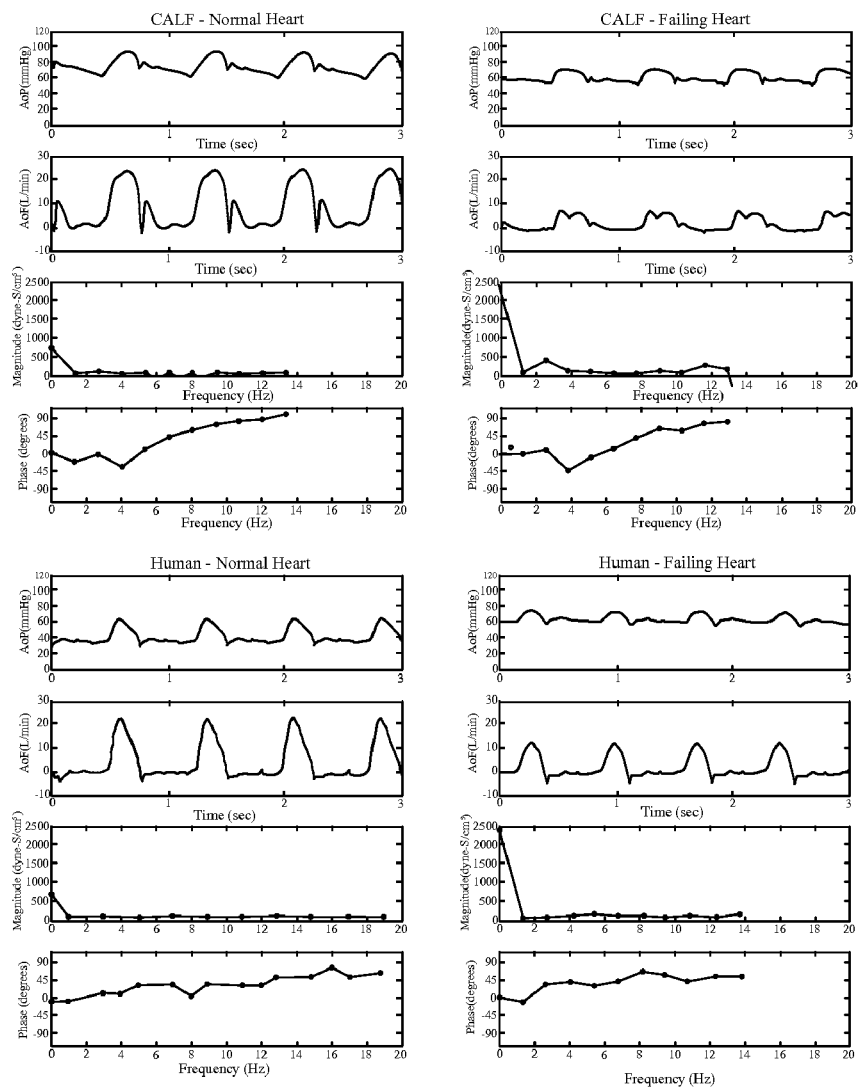
FIG. 18 is a comparison of graphs showing aortic pressure (AoP) and aortic flow (AoF) as a function of time, and magnitude and phase as a function of frequency, for normal and failing calf and human hearts.
Figure 19:
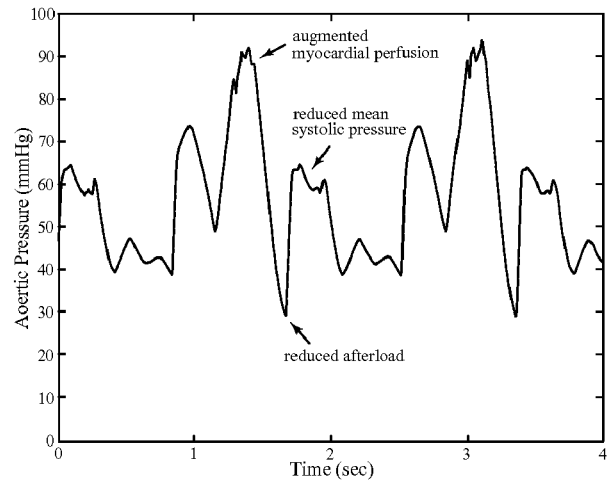
FIG. 19 is a graph showing change in aortic pressure as a function of time in an acute large animal heart failure model.
Figure 20:
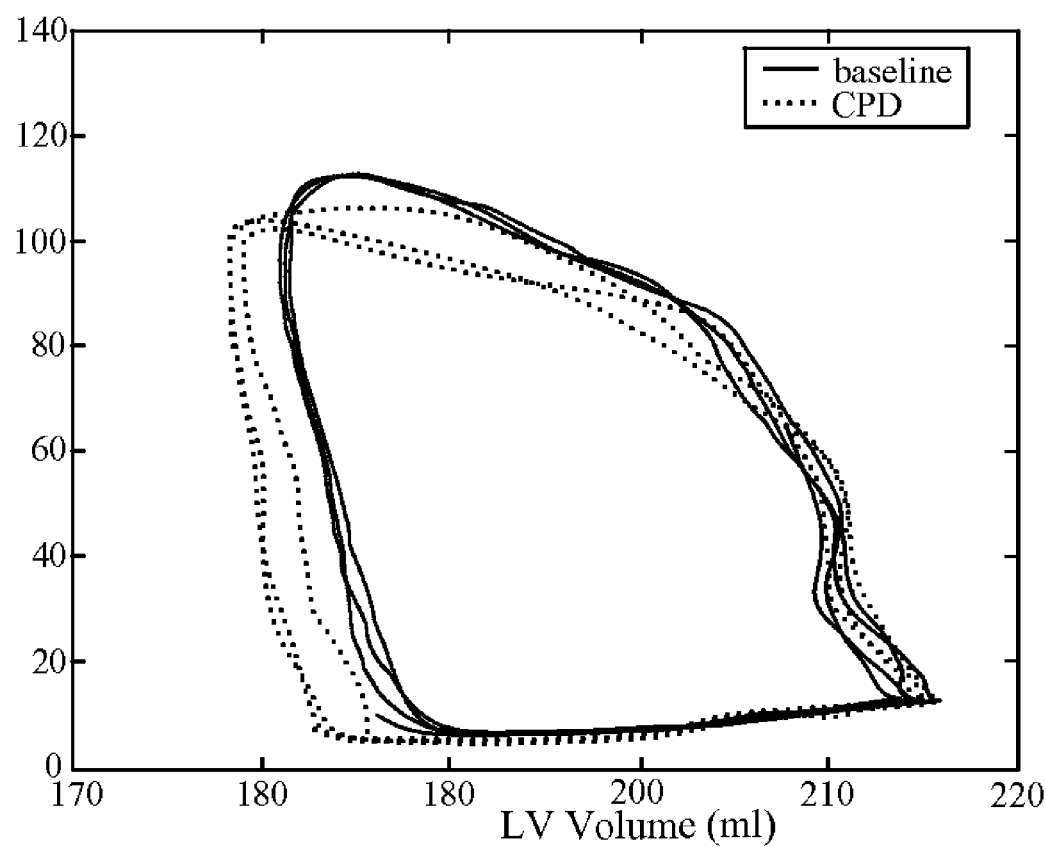
FIG. 20 is a graph comparing the pressure-volume relationship in the DCF calf model before and after treatment.

Data obtained in calves with normal and DCF hearts are used to calculate the systemic vascular input impedance (afterload). FIG. 18 compares various graphs showing Aortic pressure (AoP) and Aortic flow (AoF) as a function of time, and magnitude and phase as a function of frequency for normal and failing calf and human hearts. These data in FIG. 18 demonstrate about a three-fold increase in the magnitude modulus and early zero-cross over phase in the DCF calves, indicative of a stiffer vasculature, thereby increasing the afterload seen by the ejecting heart and reducing the amount of diastolic blood flow to the heart. These data are comparable to clinical measurements obtained in patients with normal and failing ventricles. The system of the proposed invention, using counterpulsation therapy in DCF calves, will restore the vascular input impedance to normal ranges.

In summary, the exemplary studies, including computer simulation and mock circulation, demonstrate the physiologic benefits of a system of the present invention, which include, for example lower ventricular workload and increased coronary flow.

It will be obvious to those skilled in the art that further modifications may be made to the embodiments described herein without departing from the spirit and scope of the present invention.

What is claimed is:

1. A system for providing cardiac support to a patient and for promoting myocardial repair and recovery, comprising:
   a device for connecting to a vasculature of the patient, including
      a pump defining a blood-receiving volume, and
      a cannula in fluid communication with said blood-receiving volume for connecting to the vasculature of the patient such that said blood-receiving volume may receive blood from and return blood to the vasculature of the patient through said cannula; and
   a control module, for controlling the device, including
      a means for establishing user-defined parameters to (a) control flow of blood from the heart to the device, wherein said user-defined parameters are directed to a selected timing and morphology for filling the device with blood so as to promote myocardial repair and recovery, and (b) control flow from the device to vasculature downstream of the device, wherein said user-defined parameters are directed to a selected timing and morphology for ejecting blood from the device so as to promote myocardial repair and recovery, and
      a means for operating said pump of the device, which is in communication with said means for establishing user-defined parameters such that the operation of said pump is in response to said established user-defined parameters.

2. The system of claim 1, wherein said means for establishing user-defined parameters comprises:
   a user input; and
   a controller for receiving said user-defined parameters from said user input and generating a signal for controlling said means for operating said pump.

3. The system of claim 2, wherein said user-defined parameters cause said pump to operate to alter one or more conditions selected from: left ventricle work load, left ventricular pressure, left ventricular flow, coronary pressure, coronary flow, aortic pressure and aortic flow.

4. The system of claim 2, wherein said means for establishing user-defined parameters further comprises:
   sensors for measuring or estimating the pressure and flow of blood of the patient; and
   a computer for:
      receiving said user-defined parameters from said controller;
      receiving said pressure and flow information and generating an error signal representing the difference between said user-defined parameters and said pressure and flow information; and
      communicating said error signal to said controller;
   wherein said controller adjusts said signal for controlling said means for operating said pump in response to said error signal.

5. The system of claim 2 and further comprising:
   a computer for:
      receiving said user-defined parameters from said controller;
      receiving measurements of pressure and flow of blood of the patient;
      generating an error signal representing the difference between said user-defined parameters and said pressure and flow measurements; and
      communicating said error signal to said controller;
   wherein said controller adjusts said signal for controlling said means for operating said pump in response to said error signal.

6. The system of claim 1, wherein the means for operating the pump includes:
   a motor; and
   a driver in communication with and operated by said motor, said driver in communication with said pump for operating said pump.

7. The system of claim 1, wherein said user-defined parameters include one or more parameters selected from:
   impedance that the left ventricle must overcome during ventricular systole;
   timing of the filling of the device;
   timing of the ejection of the device;
   morphology of the filling of the device;
   morphology of the ejection of the device;
   rate of change of pressure during filling of the device;
   rate of change of pressure during ejection of the device;
   volume accepted by the device;
   volume ejected by the device;
   rate of change of volume accepted by the device;
   rate of change of volume ejected from the device; and
   ratio of the number of assisted heart beats to the total number of heart beats.

8. The system of claim 1, wherein said control module additionally comprises a valve for controlling the flow of blood downstream of said pump.

9. A system for providing cardiac support to a patient and for promoting myocardial repair and recovery, comprising:
   a device adapted to fill with blood from a vasculature of the patient during native heart systole and return blood to the vasculature during diastole in accordance with one or more user-defined parameters to (a) control flow of blood from the heart to the device, wherein said user-defined parameters are directed to a selected timing and morphology for filling the device with blood, and (b) control flow from the device to vasculature downstream of the device, wherein said user-defined parameters are directed to a selected timing and morphology for ejecting blood from the device, selected from the parameters comprising:

impedance that the left ventricle must overcome during native heart systole;
timing of the filling of the device;
timing of the ejection of the device;
morphology of the filling of the device;
morphology of the ejection of the device;
rate of change of pressure during filling of the device;
rate of change of pressure during ejection of the device;
volume accepted by the device;
volume ejected by the device;
rate of change of volume accepted by the device;
rate of change of volume ejected from the device; and
ratio of the number of assisted heart beats to the total number of heart beats;
wherein the left ventricle of the heart of the patient is allowed to fill with and eject a normal or a user-defined volume of blood.

10. The system of claim 9 and further comprising:
a user input; and
a controller for receiving said user-defined parameters from said user input and generating a signal for controlling the device in accordance with said user-defined parameters.

11. The system of claim 10 wherein said device comprises:
a pump defining a blood-receiving volume; and
a means for placing said blood-receiving volume in fluid communication with the vasculature of the patient.

12. The system of claim 10 and further comprising:
a computer for:
receiving said user-defined parameters from said controller;
receiving measurements of pressure and flow of blood of the patient;
generating an error signal representing the difference between said user-defined parameters and said pressure and flow measurements; and
communicating said error signal to said controller;
wherein said controller adjusts said signal for controlling said device in response to said error signal.

13. The system of claim 12 and further comprising sensors for directly measuring or estimating pressure and flow of blood of the patient, wherein said computer receives measurements of pressure and flow of blood of the patient from said sensors.

14. A method for providing cardiac support to a patient and for promoting myocardial repair and recovery, comprising:
providing a system including a device for receiving blood from and returning blood to a vasculature of the patient while allowing the heart to fill and eject normal volumes of blood, and a control module for controlling the device in accordance with user-defined parameters to (a) control flow of blood from the heart to the device, wherein said user-defined parameters are directed to a selected timing and morphology for filling the device with blood; and (b) control flow from the device to vasculature downstream of the device, wherein said user-defined parameters are directed to a selected timing and morphology for ejecting blood from the device;
identifying one or more desired alterations to the heart of the patient and/or the vasculature of the patient; and
selecting one or more of said user-defined parameters to affect the identified one or more desired alterations.

15. The method of claim 14, wherein the one or more desired alterations to the heart of the patient and/or the vasculature of the patient include: change in left ventricle work load, change in left ventricular pressure, change in left ventricular flow, change in coronary pressure, change in coronary flow, change in aortic pressure and change in aortic flow.

16. The method of claim 14, wherein the one or more user-defined parameters include: impedance that the left ventricle must overcome during ventricular systole; timing of the filling of the device; timing of the ejection of the device; morphology of the filling of the device; morphology of the ejection of the device; rate of change of pressure during filling of the device; rate of change of pressure during ejection of the device; volume accepted by the device; volume ejected by the device; rate of change of volume accepted by the device; rate of change of volume ejected from the device; and ratio of the number of assisted heart beats to the total number of heart beats.

17. The method of claim 14 and further comprising: adjusting said one or more user-defined parameters during the course of the cardiac support.

18. The method of claim 14 and further comprising:
measuring pressure and flow of blood of the patient;
calculating an error representing the difference between said user-defined parameters and the pressure and flow measurements; and
adjusting said user-defined parameters to obtain a desired error or to substantially eliminate the error.

19. The method of claim 14 and further comprising:
obtaining first measurements of pressure and flow of blood of the patient;
adjusting said one or more user-defined parameters during the course of the cardiac support;
obtaining second measurements of pressure and flow of blood of the patient; and
assessing a degree of myocardial repair and recovery by correlating a change between said first and second measurements of pressure and flow of blood of the patient.

20. A method of controlling a blood pump device having a cannula connected to a patient's vasculature downstream of the left ventricle such that the blood pump device can fill with blood during native heart systole and return blood during diastole, said method comprising:
receiving user defined user-defined parameters to (a) control flow of blood from the heart to the device, wherein said user-defined parameters are directed to a selected timing and morphology for filling the device with blood; and (b) control flow from the device to vasculature downstream of the device, wherein said user-defined parameters are directed to a selected timing and morphology for ejecting blood from the device, for operation of said blood pump device, and
generating a signal for controlling said blood pump device in accordance with said selected user-defined parameters.

21. The method of claim 20, wherein said user-defined parameters are selected from the parameters comprising:
impedance that the left ventricle must overcome during ventricular systole;
timing of the filling of the device;
timing of the ejection of the device;
morphology of the filling of the device;
morphology of the ejection of the device;
rate of change of pressure during filling of the device;
rate of change of pressure during ejection of the device;
volume accepted by the device;
volume ejected by the device;
rate of change of volume accepted by the device;
rate of change of volume ejected from the device; and
ratio of the number of assisted heart beats to the total number of heart beats.

22. The method of claim 21, wherein at least one of the following patient characteristics are affected: left ventricle work load; left ventricular pressure, left ventricular flow, coronary pressure, aortic pressure, and aortic flow.

23. The method of claim 22, and further comprising:
   measuring pressure and flow of blood of the patient;
   relating said pressure and flow measurements to characteristics corresponding to said user-defined parameters; and
   calculating an error representing the difference between said user-defined parameters and the characteristics represented by said pressure and flow measurements.

24. The method of claim 23, and further comprising adjusting said signal for controlling said blood pump device to reduce said error.

25. The method of claim 24, and further comprising controlling the flow of blood downstream of said pump.

26. A system for providing cardiac support to a patient and for promoting myocardial repair and recovery, comprising:
   a device for connecting to a heart of the patient, including
      a pump defining a blood-receiving volume, and
      a cannula in fluid communication with said blood-receiving volume for connecting to the heart of the patient such that said blood-receiving volume may receive blood from and return blood to the heart of the patient through said cannula; and
   a control module, for controlling the device, including
      a means for establishing user-defined parameters to (a) control flow of blood from the heart to the device, wherein said user-defined parameters are directed to a selected timing and morphology for filling the device with blood so as to promote myocardial repair and recovery, and (b) control flow from the device, wherein said user-defined parameters are directed to a selected timing and morphology for ejecting blood from the device so as to promote myocardial repair and recovery, and
      a means for operating said pump of the device, which is in communication with said means for establishing user-defined parameters such that the operation of said pump is in response to said established user-defined parameters.

27. A system for providing cardiac support to a patient and for promoting myocardial repair and recovery, comprising:
   a device for connecting to a vasculature of the patient, including
      a pump defining a blood-receiving volume, and
      a cannula in fluid communication with said blood-receiving volume for connecting to the vasculature of the patient such that said blood-receiving volume may receive blood from and return blood to the vasculature of the patient through said cannula; and
   a control module, for controlling the device, including
      a means for establishing an input impedance profile, which defines an impedance experienced by the left ventricle of the heart of the patient so as to promote myocardial repair and recovery, and
      a means for operating said pump of the device, which is in communication with said means for establishing the input impedance profile such that the operation of said pump is in response to the input impedance profile.

* * * * *

UNITED STATES PATENT AND TRADEMARK OFFICE
CERTIFICATE OF CORRECTION

| | | |
|---|---|---|
| PATENT NO. | : 7,572,217 B1 | Page 1 of 1 |
| APPLICATION NO. | : 11/152872 | |
| DATED | : August 11, 2009 | |
| INVENTOR(S) | : Koenig et al. | |

It is certified that error appears in the above-identified patent and that said Letters Patent is hereby corrected as shown below:

IN THE CLAIMS:

Claim 20, col. 20, line 40: Delete the words "user defined"

Signed and Sealed this

Twenty-ninth Day of September, 2009

David J. Kappos
*Director of the United States Patent and Trademark Office*

UNITED STATES PATENT AND TRADEMARK OFFICE
CERTIFICATE OF CORRECTION

PATENT NO. : 7,572,217 B1
APPLICATION NO. : 11/152872
DATED : August 11, 2009
INVENTOR(S) : Koenig et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 640 days.

Signed and Sealed this

Seventh Day of September, 2010

David J. Kappos
*Director of the United States Patent and Trademark Office*